United States Patent

Schraga

[11] Patent Number: 6,022,366
[45] Date of Patent: Feb. 8, 2000

[54] LANCET HAVING ADJUSTABLE PENETRATION DEPTH

[75] Inventor: Steven Schraga, Surfside, Fla.

[73] Assignee: Stat Medical Devices Inc., North Miami, Fla.

[21] Appl. No.: 09/095,902

[22] Filed: Jun. 11, 1998

[51] Int. Cl.[7] ............................. A61B 17/14; A61B 17/32
[52] U.S. Cl. ......................................... 606/181; 6065/182
[58] Field of Search .................................... 606/181, 182, 606/183, 167

[56] References Cited

U.S. PATENT DOCUMENTS

| | | |
|---|---|---|
| 1,135,465 | 4/1915 | Pollock . |
| 4,388,925 | 6/1983 | Burns . |
| 4,426,105 | 1/1984 | Plaquin et al. . |
| 4,785,858 | 11/1988 | Valentini . |
| 4,834,667 | 5/1989 | Fowler et al. . |
| 4,858,607 | 8/1989 | Jordan et al. . |
| 4,895,147 | 1/1990 | Bodicky et al. . |
| 4,924,879 | 5/1990 | O'Brien . |
| 5,304,193 | 4/1994 | Zhadanov . |
| 5,318,584 | 6/1994 | Lange et al. . |
| 5,324,303 | 6/1994 | Strong et al. . |
| 5,454,828 | 10/1995 | Schraga . |
| 5,464,418 | 11/1995 | Schraga . |
| 5,554,166 | 9/1996 | Lange et al. . |
| 5,569,287 | 10/1996 | Tezuka et al. . |
| 5,613,978 | 3/1997 | Harding . |
| 5,628,764 | 5/1997 | Schraga . |
| 5,628,765 | 5/1997 | Morita . |
| 5,730,753 | 3/1998 | Morita . |
| 5,916,230 | 6/1999 | Brenneman et al. .................... 606/182 |

FOREIGN PATENT DOCUMENTS

| | | |
|---|---|---|
| 523078 | 3/1956 | Canada . |

OTHER PUBLICATIONS

Sutor et al., "Bleeding from Standardized Skin Punctures: Automated Technic for Recording Time, Intensity, and Pattern of Bleeding", A.J.C.P., vol. 55, pp. 541–549 (May 1971).

*Primary Examiner*—Michael Buiz
*Assistant Examiner*—Vy Q. Bui
*Attorney, Agent, or Firm*—Greenblum & Bernstein, P.L.C.

[57] ABSTRACT

Lancet device having an adjustable penetration depth. The lancet device includes a housing, a cap for covering the housing and for positioning the lancet device relative to a skin surface, a needle holding member for holding a lancet which needle holding member is at least partially contained within the housing, a biasing element for biasing the needle holding member toward an extended position, and a trigger for releasing the needle holding member from a retracted position. The lancet device further includes a mechanism for adjusting a penetration depth of a lancet. The penetration depth adjustment mechanism may involve adjusting a travel distance of the needle holding member, wherein the mechanism is positioned within at least one of the housing and the cap during at least a portion of length of travel of the needle holding member. The penetration depth adjustment mechanism may involve adjusting a travel distance of the needle holding member by adjusting a length of the needle holding member. The penetration depth adjustment mechanism may involve aligning at least one stop of the housing with at least one protrusion of the needle holding member. The penetration depth adjustment mechanism may involve a cavity in the needle holding member for holding a lancet, wherein the cavity depth of the needle holding member is adjusted.

21 Claims, 17 Drawing Sheets

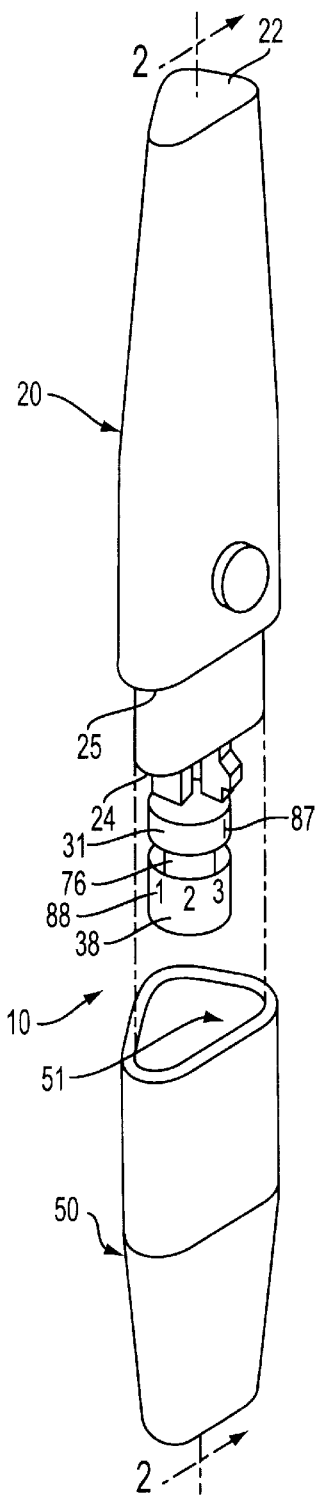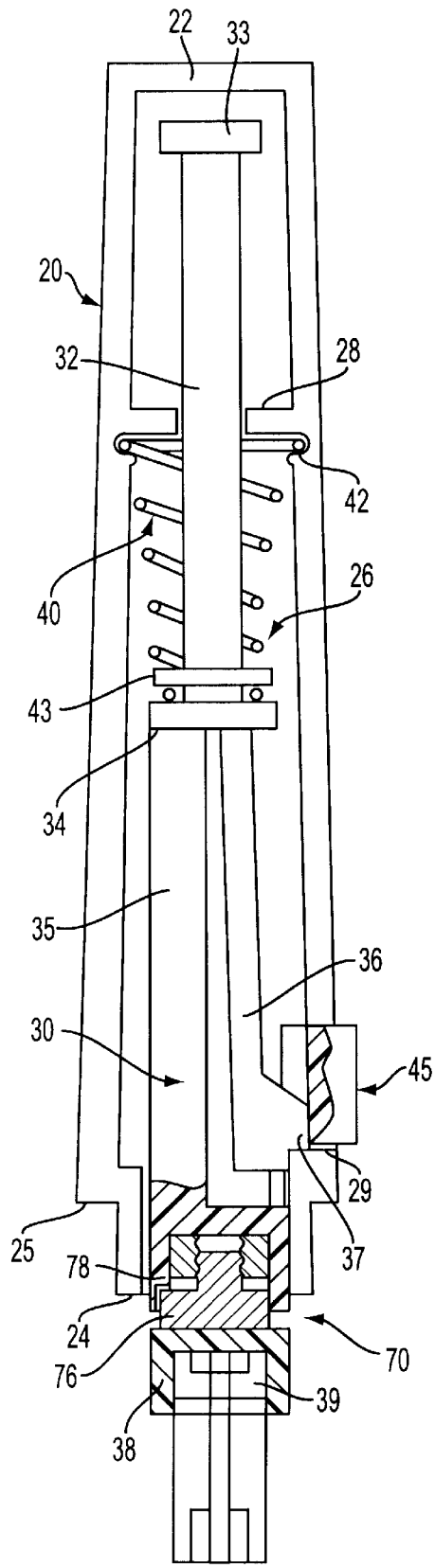
FIG. 1
FIG. 2

LANCET HAVING ADJUSTABLE PENETRATION DEPTH

CROSS-REFERENCE TO RELATED APPLICATIONS

The present application expressly incorporates by reference herein the entire disclosure of Attorney Docket No. P16687, U.S. Application No. 09/095,905, entitled "Adjustable Length Member Such as a Cap of a Lancet Device for Adjusting Penetration Depth", which is concurrently filed with the present application.

BACKGROUND OF THE INVENTION

1. Field of the Invention

The present invention relates to a lancet device whose penetration depth is adjustable. The lancet device is adapted to be substantially inexpensive to manufacture and easy and safe to use by physically impaired individuals who take their own blood samples.

2. Description of Background Information

The field relating to disposable and reusable lancet devices is substantially crowded. U.S. Pat. No. 5,464,418 to SCHRAGA, the disclosure of which is incorporated by reference herein in its entirety, discloses a reusable lancet device having an elongate triangular housing and triangular cap segment.

Lancets which allow adjustment of the penetration depth include U.S. Pat. No. 5,318,584 to LANGE et al., the disclosure of which is incorporated by reference herein in its entirety. This document discloses a blood lancet device for withdrawing blood for diagnostic purposes. The penetration depth of this blood lancet device may be adjusted by adjusting the position of a sealing cap relative to a housing.

U.S. Pat. No. 4,924,879 to O'BRIEN, the disclosure of which is incorporated by reference herein in its entirety, discloses a blood lancet device. The penetration depth may be adjusted by adjusting the position of a skin surface sensor which may be a small socket head screw.

U.S. Pat. No. 5,613,978 to HARDING, the disclosure of which is incorporated by reference herein in its entirety, discloses an adjustable tip for a lancet device. The penetration depth of this lancet may be adjusted by adjusting the position of an outer cylindrical sleeve relative to an inner sleeve.

U.S. Pat. No. 4,895,147 to BODICKY et al., the disclosure of which is incorporated by reference herein in its entirety, discloses a lancet injector which includes an elongate tubular housing with a penetration depth selector provided thereon. Rotation of the penetration depth selector causes a control member to contact different contact edges to thereby control the distance that a lancet tip protrudes through a central opening.

U.S. Pat. No. 1,135,465 to POLLOCK, the disclosure of which is incorporated by reference herein in its entirety, discloses a lancet. The distance that a plunger is allowed to move forward may be changed by an adjustable movement limiting or regulating collar.

Canadian Patent No. 523,078, the disclosure of which is incorporated by reference herein in its entirety, discloses a surgical device for use in the treatment of snake bites. The surgical device includes a lance or blade whose penetration depth may be adjusted by inserting or removing a stop bar from the path of the lance or blade.

SUTOR et al., "Bleeding from Standardized Skin Punctures: Automated Technic for Recording Time, Intensity, and Pattern of Bleeding", A.J.C.P., Vol. 55, pp. 541–549 (May 1971), the disclosure of which is incorporated by reference herein in its entirety, discloses a Mayo automatic lancet. A knurled thumb screw allows adjustment of depth of cut by regulating distance between a plunger and a striking head by means of a millimeter scale.

Although there are several devices which allow adjustment of the penetration depth, there are important factors relating to the safe and effective use of lancet assemblies which have not been addressed by such devices. Specifically, there is a need for a lancet device having an adjustable penetration depth whose penetration depth adjustment mechanism is reliable and difficult to accidentally change.

SUMMARY OF THE INVENTION

The present invention is directed toward a lancet device, such as a reusable lancet device, to be utilized with a lancet whose penetration depth is adjustable.

It is an object of the present invention to provide a lancet device which has an adjustable penetration depth. The penetration depth may be adjusted by adjusting the length of a needle holding member, by adjusting the length of a housing, by adjusting the position of a stop, and/or by adjusting the depth of a cavity of a proximal segment of a needle holding member.

It is another object of the present invention to provide a lancet device having a penetration depth adjustment mechanism which is contained entirely within a housing to reduce the possibility of accidental misadjustment of the penetration.

It is another object of the present invention to provide a lancet device having a penetration depth adjustment mechanism with a simplified cap construction.

It is an object of the present invention to provide a lancet device which is substantially cost effective to manufacture due to a small number of individual pieces to be put together, yet will still be substantially safe during use.

Still another object of the present invention is to provide a lancet device which provides for facilitated and effective cap positioning by impaired individuals.

Yet another object of the present invention is to provide a lancet device which is comfortably positionable within a user's hand and will not roll around within a user's hand or on a flat surface.

A further object of the present invention is to provide an improved lancet device which does not necessitate that an exteriorly exposed plunger assembly be utilized in order to position the lancet in a retracted, ready-to-use position.

Further, the device of the present invention is designed to be utilized by individuals to do their own routine blood test such as individuals who do home monitoring of their blood such as diabetes patients. As a result, the present invention requires precise adaptation to make it effective yet safe for the user. As a result, the device of the present invention is comprised of a small number of individual pieces, thereby making the lancet device easier and substantially more cost effective to manufacture and provide for use by patients, without compromising any of the safety needs and in fact increasing the safety of use.

In accordance with one aspect, the present invention is directed to a lancet device, including: a housing; a cap for covering the housing and for positioning the lancet device relative to a skin surface; a needle holding member for holding a lancet, the needle holding member being at least partially contained within the housing; a biasing element for biasing the needle holding member toward an extended position; a trigger for releasing the needle holding member from a retracted position; and a travel adjustment mechanism capable of adjusting a length of travel of said needle holding member, said travel adjustment mechanism being positioned within at least one of said housing and said cap during at least a portion of the length of travel of said needle holding member. The travel adjustment mechanism may be completely positioned or completely contained within at least one of the housing and the cap during at least a portion of the length of travel of the needle holding member.

In accordance with another aspect, the needle holding member comprises a first component and a second component, and the travel adjustment mechanism comprises a threaded connection between the first component and the second component. The travel adjustment mechanism may further include a protruding element on one of the first component and the second component, and grooves on the other of the first component and the second component, with the protruding element being capable of engaging the grooves. The protruding element may comprise a nipple or a spring-biased ball.

In accordance with yet another aspect, the needle holding member comprises a first component and a second component, and the travel adjustment mechanism comprises a spring-biased element on one of the first component and the second component, and a plurality of recesses in the other of the first component and the second component, with the spring-biased element being capable of engaging the recesses.

In accordance with still another aspect, the needle holding member comprises a first component and a second component, and the travel adjustment mechanism comprises grooves in one of the first component and the second component, and a ridge on the other of the first component and the second component, with the ridge being capable of engaging the grooves.

In accordance with still another aspect, the needle holding member comprises a first component and a second component, and the travel adjustment mechanism comprises grooves in one of the first component and the second component, and at least one leaf spring on the other of the first component and the second component, with the at least one leaf spring being capable of engaging the grooves.

In accordance with still another aspect, the housing comprises a plurality of stops, and the needle holding member comprises a protrusion for engaging the stops one at a time. The needle holding member and the housing may be capable of rotating relative to each other.

In accordance with another aspect, the travel adjustment mechanism is positioned within said housing and said cap during the length of travel of said needle holding member.

In accordance with another aspect, the present invention is directed to a lancet device, comprising: a housing; a cap for covering the housing and for positioning the lancet device relative to a skin surface; a needle holding member for holding a lancet, the needle holding member being at least partially contained within the housing, a length of the needle holding member being adjustable; a biasing element for biasing the needle holding member toward an extended position; and a trigger for releasing the needle holding member from a retracted position.

In accordance with another aspect, the present invention is directed to a lancet device, comprising: a housing containing at least one stop; a cap for covering the housing and for positioning the lancet device relative to a skin surface; a needle holding member for holding a lancet, the needle holding member being at least partially contained within the housing, the needle holding member having at least one protrusion for striking the at least one stop of the housing; a biasing element for biasing the needle holding member toward an extended position; a trigger for releasing the needle holding member from a retracted position; and an alignment mechanism capable of aligning the at least one stop of the housing and the at least one protrusion of the needle holding member to adjust the extended position of the needle holding member.

In accordance with another aspect, the housing comprises an upper housing and a lower housing, and the alignment mechanism comprises a threaded connection between the upper housing and the lower housing. The at least one stop may comprise a guide collar on the lower housing.

In accordance with still another aspect, the housing comprises an upper housing and a lower housing, and the alignment mechanism comprises a spring between the upper housing and the lower housing to bias the lower housing into the upper housing, and the alignment mechanism comprises a spacer between the upper housing and the lower housing to act against a biasing force of the spring. The at least one stop may comprise a guide collar on the lower housing.

In accordance with yet another aspect, the housing comprises an upper housing and a lower housing, with the lower housing having the at least one stop which comprises a plurality of stops, and the alignment mechanism comprises a threaded connection between the upper housing and the lower housing. The plurality of stops may comprise stops at different radial and axial positions on an interior of the lower housing.

In accordance with another aspect, the at least one stop comprises a plurality of stops, and the alignment mechanism comprises a rotary connection between the housing and the needle holding member. The plurality of stops may comprise stops at different radial and axial positions on an interior of the housing.

In accordance with another aspect, the present invention is directed to a lancet device, comprising: a housing; a cap for covering the housing and for positioning the lancet device relative to a skin surface; a needle holding member comprising a cavity having a depth for holding a lancet, the needle holding member being at least partially contained within the housing; a biasing element for biasing the needle holding member toward an extended position; a trigger for releasing the needle holding member from a retracted position; and an adjustable member disposed within the cavity of the needle holding member for adjusting the cavity depth of the needle holding member.

In accordance with still another aspect, the adjustable member comprises a screw.

In accordance with yet another aspect, the needle holding member comprises a turn key having a pinion, and the adjustable member comprises a nail having a tail which has a rack for engaging the pinion.

In accordance with another aspect, the present invention is directed to a lancet device, comprising: a housing; a cap for covering the housing and for positioning the lancet device relative to a skin surface; a needle holding member for holding a lancet, the needle holding member being at least partially contained within the housing; a biasing element for biasing the needle holding member toward an extended position; a trigger for releasing the needle holding member from a retracted position; and means for adjusting a penetration depth of a lancet by adjusting a travel distance of the needle holding member, the means for adjusting the penetration depth being capable of being contained within the housing and the cap.

In accordance with another aspect, the present invention is directed to a lancet device, comprising: a housing; a cap for covering the housing and for positioning the lancet device relative to a skin surface; a needle holding member for holding a lancet, the needle holding member being at least partially contained within the housing; a biasing element for biasing the needle holding member toward an extended position; a trigger for releasing the needle holding member from a retracted position; and means for adjusting a penetration depth of a lancet by adjusting a length of the needle holding member.

In accordance with another aspect, the present invention is directed to a lancet device, comprising: a housing containing at least one stop; a cap for covering the housing and for positioning the lancet device relative to a skin surface; a needle holding member for holding a lancet, the needle holding member being at least partially contained within the housing, the needle holding member having at least one protrusion for striking the at least one stop of the housing; a biasing element for biasing the needle holding member toward an extended position; a trigger for releasing the needle holding member from a retracted position; and means for adjusting a penetration depth of a lancet by aligning the at least one stop of the housing and the at least one protrusion of the needle holding member.

In accordance with another aspect, the present invention is directed to a lancet device, comprising: a housing; a cap for covering the housing and for positioning the lancet device relative to a skin surface; a needle holding member comprising a cavity having a depth for holding a lancet, the needle holding member being at least partially contained within the housing; a biasing element for biasing the needle holding member toward an extended position; a trigger for releasing the needle holding member from a retracted position; and means for adjusting a penetration depth of a lancet by adjusting the cavity depth of the needle holding member.

BRIEF DESCRIPTION OF THE DRAWINGS

The present invention is further described in the detailed description which follows, in reference to the noted plurality of non-limiting drawings, and wherein:

FIG. 1 is a partially exploded perspective view of the lancet device of the present invention.

FIG. 2 is a cross-sectional view along line 2—2 of FIG. 1.

Like reference numerals refer to like parts throughout the several views of the drawings.

DETAILED DESCRIPTION

Figure 3A:
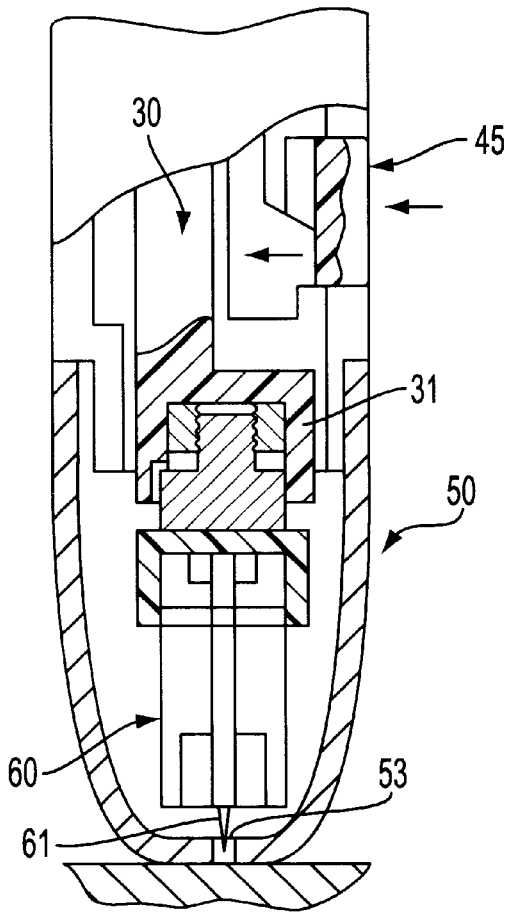
FIGS. 3A, 3B, 3C, and 3D are isolated, cross-sectional views of the lancet device illustrating the functioning of the lancet.

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

Before referring to the Figures, a broad overview of preferred aspects of the invention is provided. The lancet device includes an elongate housing, which is preferably triangular, adapted to fit within the user's hand. This housing includes a first end, which can be closed or open, an open second end, and an elongate channel therein which extends from the first end to the second end.

Disposed within this elongate channel is an elongate needle holding member. This needle holding member is movable between a cocked, retracted position and an extended position. The needle holding member is structured to hold a disposable lancet therein, such that a point thereof extends away from the needle holding member.

A biasing element is disposed within the housing. The biasing element is adapted to urge the needle holding member into an extended position for penetrating a user's skin when not held in a retracted position.

According to the present invention, there are several different embodiments for adjusting the penetration depth of the lancet, i.e., for adjusting the maximum distance which the lancet in the needle holding member extends out of the housing. The penetration depth may be adjusted by adjusting the length of the needle holding member, by adjusting the length of the housing, by adjusting the position of a stop, and/or by adjusting the depth of a cavity of the needle holding member. Adjusting the penetration depth is important because different penetration depths are necessary to draw blood from different people due to differences in skin thickness, differences in healing time of the skin puncture, differences in pain tolerances, and differences in the amount of blood needed to be drawn.

Regardless of how the penetration depth is adjusted, the present invention includes a stopper system to prevent axial movement of the needle holding member within the housing. Utilizing the stopper system, the needle holding member will always be retained within the channel despite its movement from the cocked, retracted position to the extended position.

The needle holding member is held in the cocked, retracted position, and accordingly a biasing element is held in a retracted, compressed position, until released by a trigger. The trigger releases the needle holding member from the cocked, retracted position which results in an immediate movement of the needle holding member to the extended position as a result of the functioning of the biasing element.

The lancet device also includes a cap segment, which is preferably triangular, with an open first side and a closed second side containing a piercing opening therein. The open first side is adapted to be matingly fitted over the open second end of the housing, thereby containing the needle holder member and disposable lancet therein. When in a cocked, retracted position, or after use, the needle holding member is disposed such that the point of the disposable lancet is concealed within the cap segment. During use, upon release by the trigger, the needle holding member is immediately moved to the extended position wherein the point of the disposable lancet will momentarily extend through a piercing opening into a piercing position which punctures a hole in a user's skin and then retracts back beneath the cap segment.

Moreover, before referring to the Figures, the illustrated reusable lancet device is similar to that disclosed in U.S. Pat. No. 5,464,418 to SCHRAGA, the disclosure of which is herein incorporated by reference in its entirety.

FIGS. 1–9 illustrate embodiments of the present invention which involve adjusting the penetration depth of a disposable lancet by adjusting the length of a needle holder member via a threaded connection between two segments of the needle holder member. The reusable lancet device 10 is preferably formed of a lightweight, rigid or semi-rigid, and substantially inexpensive plastic material and is adapted for use with a standard type of disposable lancet 60. The reusable lancet device 10 includes primarily an elongate, substantially triangular shaped housing 20. The housing 20 includes the substantially triangular shape, with slightly rounded corners, such that it will be easy to manipulate and will not unnecessarily roll around within a user's hand, especially if the user is sick, old, or otherwise impaired. Although the most preferred shape of the housing 20 is triangular, the housing 20 may be other shapes such as round but is preferably any shape that will not roll around on a flat surface such as D-shaped, rectangular, or octagonal.

The elongate triangular housing 20, as illustrated in FIG. 2, includes a closed first end 22, an open second end 24, and an elongate channel 26. Further, the housing 20 is preferably molded of two halves to be joined together, so as to facilitate manufacture. The elongate channel 26 extends from the closed first end 22 to the open second end 24.

Slidably positioned within the channel 26 is an elongate needle holding member 30. This needle holding member 30, which is movable between a cocked, retracted position, illustrated in FIG. 2, and an extended position, illustrated in FIG. 3B, includes four segments. Specifically, the needle holding member 30 is formed of a distal segment 32, a distal central segment 35, a proximal central segment 31, and a proximal segment 38.

The proximal segment 38 and the proximal central segment 31 cooperate to form an adjustment mechanism 70 for adjusting the length of the needle holding member 30. The length adjustment mechanism 70 involves a threaded connection between the proximal segment 38 and the proximal central segment 31. The proximal segment 38 includes external threads 72 and the proximal central segment 31 includes internal threads 74 for engaging each other. In an alternative embodiment which is not shown in the drawings, the threading is reversed such that the proximal segment 38 has internal threading and the proximal central segment 31 has external threading.

To allow the length of the needle holding member to be set at a particular length, the threaded length adjustment mechanism includes a protruding element 76 on the proximal segment 38 which engages grooves 78 on the proximal central segment 31. The protruding element 76 is shown as a single nipple but may be more than one nipple and may be one or more spring-biased balls in alternative embodiments.

Figure 9:
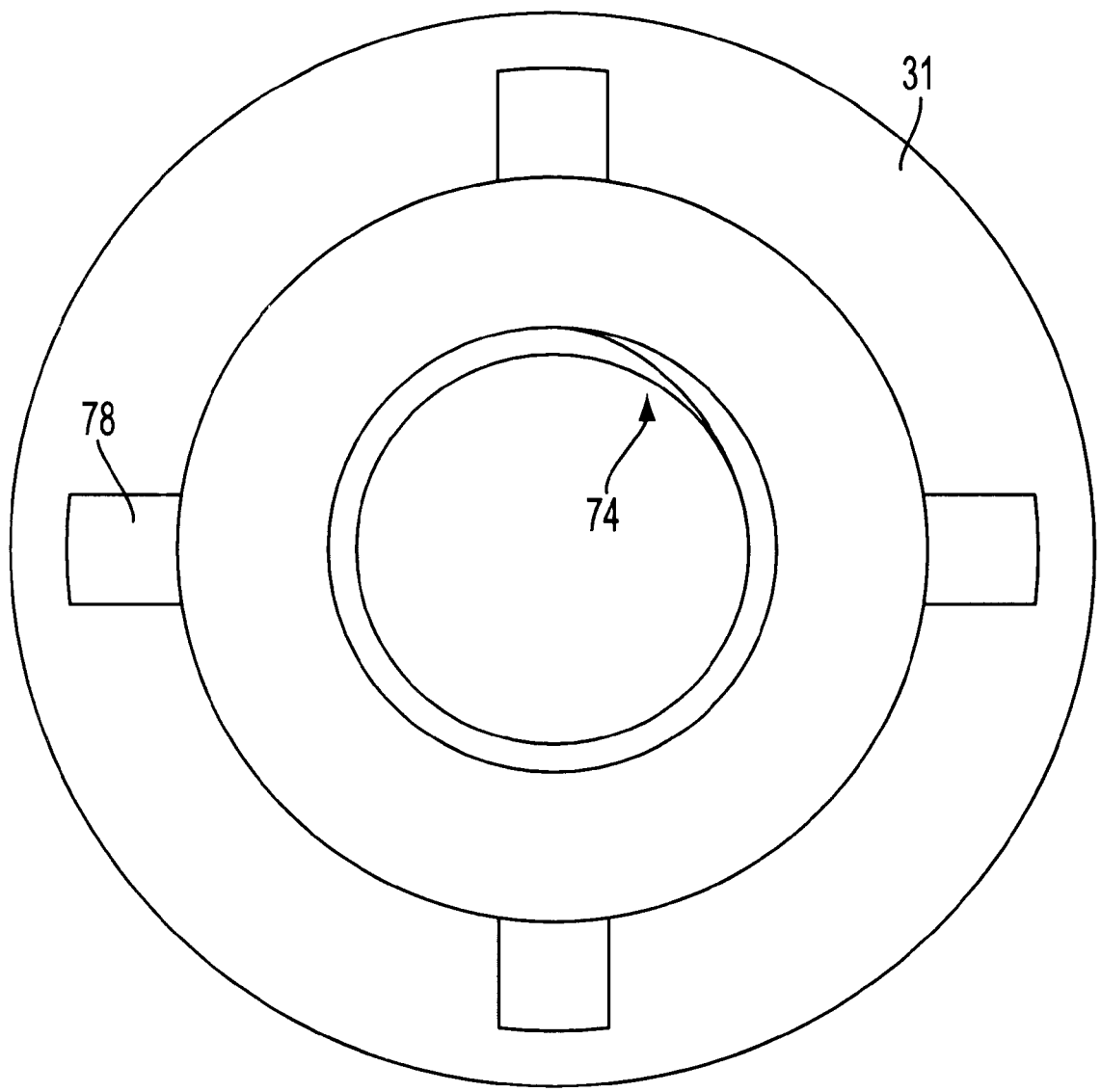
FIG. 9 is a top view of the proximal central segment of the present invention showing grooves for engaging a protruding element of the proximal segment.

Upon rotation of the proximal segment 38 and the proximal central segment 31 relative to each other about the threaded connection of the length adjustment mechanism 70, the overall length of the needle holding member 30 is increased or decreased depending upon the direction of rotation. During rotation, the protruding element 76 snaps into and out of grooves 78 such that the length of the needle holding member may be fixed at a particular length by leaving the protruding element 76 engaged in a particular groove 78. FIG. 9 shows how the grooves 78 and internal threads 74 are positioned within the interior of the proximal central segment 31. Other techniques for setting the position of threaded elements may also be used to fix the length of the needle holding member 30, such as using a set screw, using washers, or using screws often used on bicycles which have nylon inserts for deterring rotation of the screw.

The proximal segment 38, which protrudes from the open second end 24 of the housing 20 is adapted to hold the disposable lancet 60 therein. Specifically, the disposable lancet 60 includes a main body 65 and a point 61, which until use is contained within a protective cap 62. When used, the body 65 is inserted into a cavity 39 of the proximal segment 38, as illustrated in FIG. 2, then the protective cap 62 is pulled or twisted from the point 61. Although the cavity 39 and disposable lancet 60 are shown as being round, the cavity 39 and disposable lancet 60 could be any other shapes, such as square, octagonal, etc., so long as the disposable lancet can be engaged in the cavity 39. The disposable lancet 60 is held in the proximal segment 38 such that the point 61 points away from the housing and such that sliding movement of the needle holding member 30 will result in corresponding movement of the disposable lancet 60.

The overall sliding and axial movement of the needle holding member 30 is regulated by a stopper system. In the preferred embodiment, detailed in FIG. 2, the stopper system includes a guide collar 28 disposed within the housing 20. The guide collar 28 is adapted to receive the distal segment 32 of the needle holding member 30 slidably theretllrough. The needle holding member 30 is preferably flat such that it will slide through the guide collar 28, but will not rotate axially therein, thereby assuring that the needle holding member 30 will remain properly oriented when moved into its cocked, retracted position. Further, the guide collar 28 is sized to retain a flanged end 33 of the distal segment 32 of the needle holding member 30 between the closed first end 22 of the housing 20 and the guide collar 28. In this manner, inward movement of the needle holding member within the housing 20 is limited by the flanged end 33 contacting the closed first end 22 of the housing 20, and outward movement of the needle holding member 20 is limited by the flanged end 33 of the distal segment 32 contacting the guide collar 28. In this manner, the needle holding member 30 will be retained within the channel 26.

Figure 8:
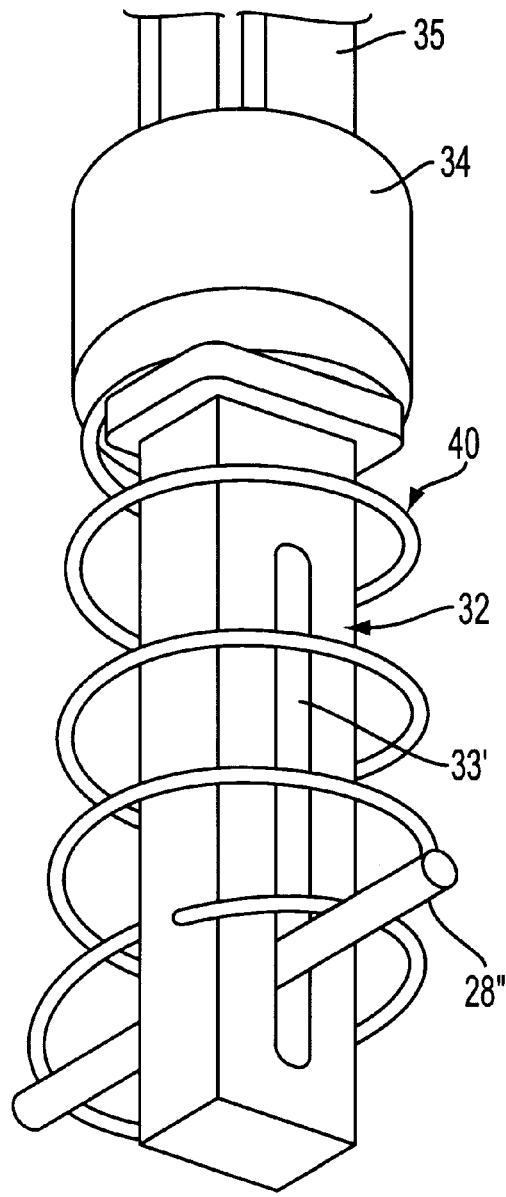
FIG. 8 is an isolated perspective view of a second embodiment of the stopper of the lancet device.

Turning to FIG. 8, an alternative embodiment of the stopper system includes an elongate slot 33' disposed in the distal segment 32 of the needle holding member 30. The slot is positioned such that a peg 28" which extends from an interior of the housing 20 passes therethrough. The peg 28" remains within the elongate slot 33' at all times thereby limiting movement of the needle holding member 30 to a length of the slot 33' and assuring that the needle holding member 30 is retained within the channel 26 of the housing 20. Also, positioning of the peg 28" within the slot 33' will not allow axial rotation of the needle holding member 30.

Figure 7:
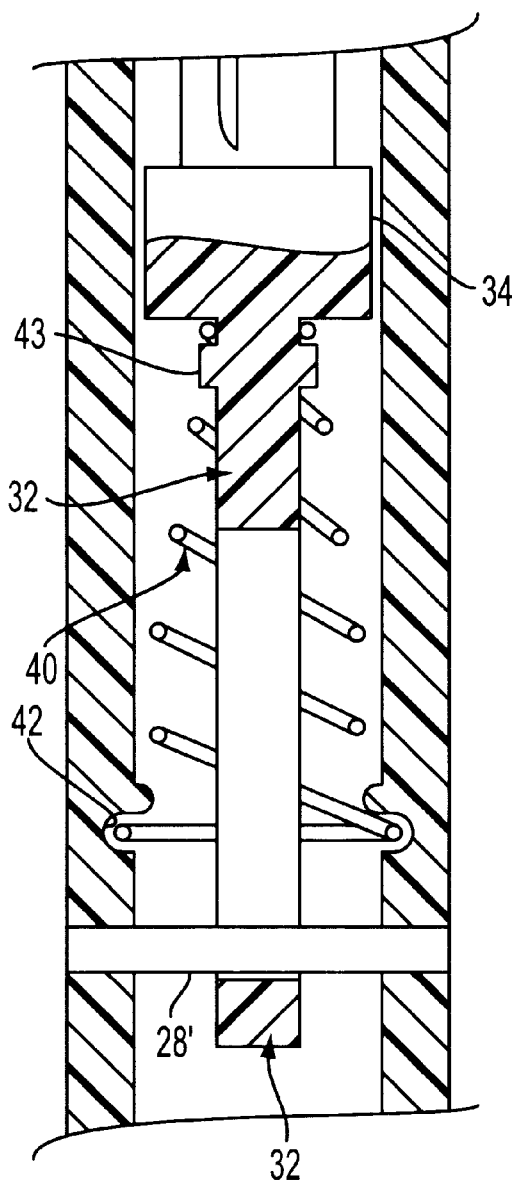
FIG. 7 is an isolated cross-sectional view illustrating the positioning of the biasing element of the lancet device according to one embodiment of the present invention, wherein the needle holding member is shown in its fully extended position.

Although the stopper systems of FIGS. 7 and 8 involve an interaction between the distal segment 32 of the needle holding member 30 and a stationary element, the stopper system could involve an interaction between another segment of the needle holding member and a stationary element. For instance, the stopper system could involve interaction of the distal central segment 35 with an element attached to the housing 20.

So as to contain and shield the exposed point 61 of the disposable lancet 60, a triangular cap segment 50 is included. The triangular cap segment 50 includes an open first side 51 and a closed second side 52. The cap segment 50 is adapted to have substantially the same configuration as the housing 20 and is sized such that the open first side 51 may be matingly fitted over the open second end 24 of the housing 20. Of course, although the cap segment 50 is shown as being triangular, the cap segment 50 may be other shapes depending upon the shape of the housing 20.

Further, the open second end 24 of the housing 20 extends from a lip 25 formed in the housing 20, the lip 25 being disposed such that the open first side 51 of the cap segment 50 slides onto the housing 20 over the open second end 24 of the housing 20 and will abut the lip 25 providing a smooth contoured finish. The cap segment 50 will be removably fitted on the housing 20 preferably through corresponding proportioning of an interior dimension of the open first side 51 of the cap segment 50 relative to the open second end 24 of the housing 20, but alternatively engagement ridges or a similar removable fastener system may be included to secure the cap segment 50 on the housing 20. Other removable fastener systems include threads, locking clips, and locking buttons.

Figure 3B:
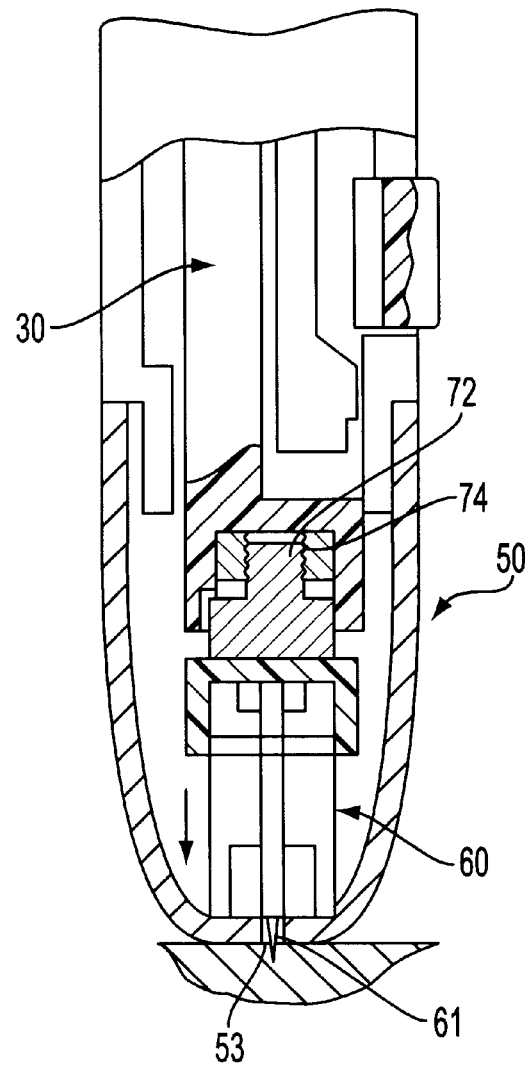

Disposed in the closed second side 52 of the cap segment 50 is a piercing opening 53. The piercing opening 53 is positioned such that when the needle holding member 30, containing a disposable lancet 60 therein, is moved to its fully extended position, the point 61 of the disposable lancet 60 will protrude through the piercing opening 53 to puncture a desired surface. FIG. 3B shows the needle holding member 30 in its fully extended position with the length of the needle holding member 30 adjusted such that the disposable lancet 60 will strike the cap segment 50 in the fully extended position.

Figure 3C:
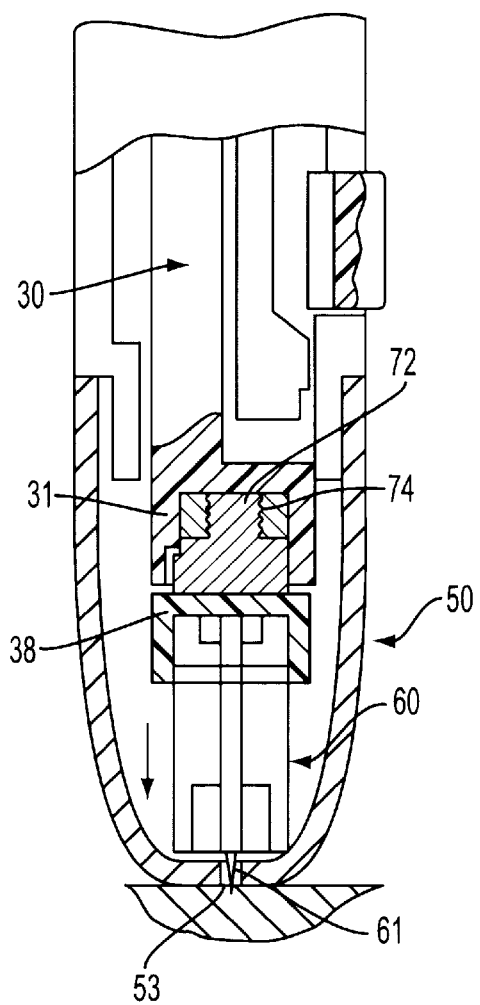

FIG. 3C also illustrates the needle holding member 30 in its fully extended position. The length of the needle holding member 30, however, has been shortened such that the disposable lancet 60 does not strike the cap segment 50 in the fully extended position. Thus, adjusting the length of the needle holding member 30 adjusts the penetration depth of the disposable lancet 60.

So as to move the needle holding member 30 from its cocked, retracted position to its fully extended position, a biasing element is included. While other types of biasing elements may be used, the biasing element is preferably in the form of a coil spring 40 disposed about the distal segment 32 of the needle holding member 30. Other types of springs which may be useful as biasing elements include leaf springs and C-springs. The spring 40 is positioned such that it will abut a flanged lip 34 formed in the needle holding member 30 and will abut the housing 20. Preferable a side of the spring 40 which abuts the housing 20 will have a larger relaxed diameter than an opposite side of the spring 40. In a first embodiment, illustrated in FIG. 2, one end of the spring 40 is positioned to contact the guide collar 28 of the housing 20 and is preferably embedded in an annular ridge 42 formed in the housing 20. The opposite side of the spring 40, which abuts the needle holding member 30 is preferably contained within an annular ridge 43 formed at the flanged lip 34. In the embodiment of FIGS. 1–7, the spring 40 abuts the housing 20 at peg 28' which is positioned through the slot 33' in the distal segment 32 as shown in FIG. 7. In an alternative embodiment illustrated in FIG. 8, the spring 40 abuts peg 28" which is also positioned through the slot 33' in the distal segment 32.

With the spring 40 positioned appropriately, when extended, the spring 40 will urge the needle holding member 30 toward the open second end 24 of the housing 20. When the needle holding member 30 is in its retracted, cocked position, as detailed in FIG. 2, the spring 40 is compressed. Once the needle holding member 30 is allowed to move to its extended position, the spring 40 will quickly and immediately move the needle holding member 30 to the fully extended position with the point 61 of the disposable lancet 60 protruding through the piercing opening 53 to puncture a desired surface. Depending upon how the length of the needle holding member 30 is set, the disposable lancet 60 will strike the cap segment 50, (see FIG. 3B), or will not strike the cap segment 50, (see FIG. 3C), in the fully extended position.

Figure 3D:
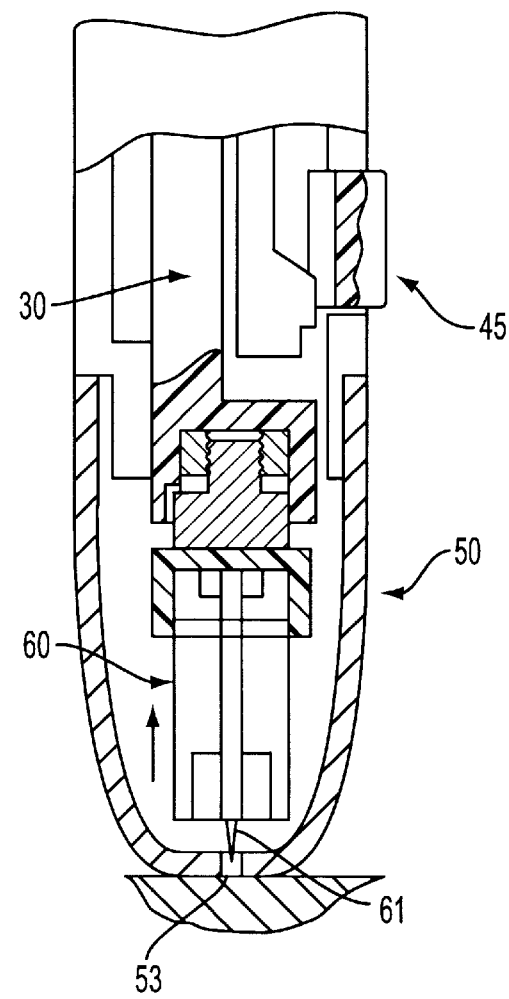
Figure 4:
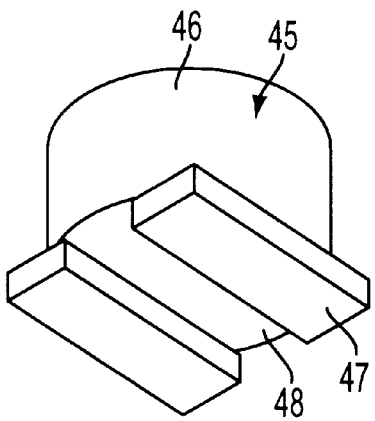
FIG. 4 is an isolated view of the trigger button of the lancet device of the present invention.
Figure 5:
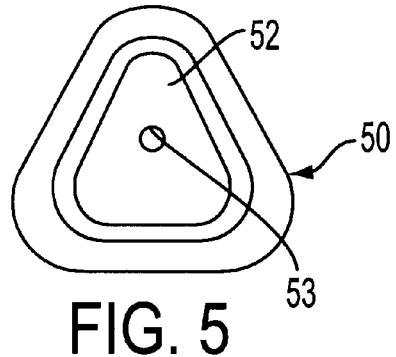
FIG. 5 is a bottom plan view of the triangular cap segment of the lancet device of the present invention.
Figure 6:
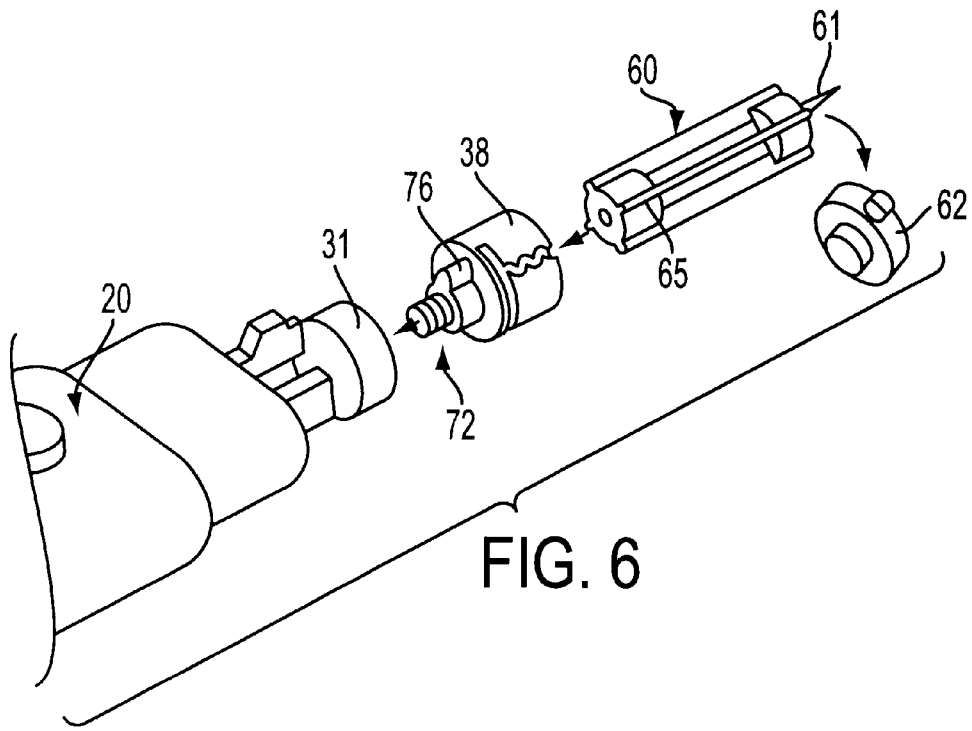
FIG. 6 is an isolated perspective view of the lancet device illustrating the positioning of a disposable lancet therein.

After this initial release and movement to the fully extended position, the spring 40 relaxes such that the needle holding member 30 will move slightly back toward the closed first end 22 of the housing 20, as illustrated in FIG. 3D, into a relaxed position wherein the point 61 of the disposable lancet 60 is contained within the cap segment 50 and will not accidentally contact a user unnecessarily.

In order to hold the needle holding member 30 in its cocked, retracted position, and subsequently allow release by a user in order to initiate movement of the needle holding member 30 to its extended position, a trigger is included. The trigger preferably includes an aperture 29 formed in the housing 20 near the open second end 24 thereof. Also included as part of the trigger is an outwardly biased engagement segment 36 which extends from the distal central segment 35 of the needle holding member 30. The engagement segment 36 includes a distal lip segment 37 which contacts an interior of the housing 20 as the needle holding member 30 slides within the channel 26. Contact is made due to the outwardly biasing nature of the engagement segment 36, and when the needle holding member 30 is pushed into the housing 20 so as to be in its retracted, cocked position, the distal lip segment 37 extends upwardly into the aperture 29 formed in the housing 20 so as to contact the housing 20 inside the aperture 29 and maintain the needle holding member 30 in its retracted, cocked position and the spring 40 in its compressed position.

In order to release the needle holding member 30 from its retracted, cocked position, the engagement segment 36 must be pushed such that the distal lip segment 37 exits the aperture 29 and the needle holding member 30 can move freely to its fully extended position due to the biasing force of the spring 40. In order to push the engagement segment 36, a trigger button 45 is disposed within the aperture 29. The trigger button 45, as detailed in FIG. 4, includes an upper section 46 which protrudes through the aperture 29 to an exterior of the housing 20 and a flanged base portion 47 which is disposed within the housing 20 so as to assure that the trigger button 45 does not get pushed out of the housing 20 through the aperture 29. Disposed within the base 47 is a channel 48 positioned such that the distal lip segment 37 of the engagement segment 36 will slide therethrough and be able to engage the housing 20 within the aperture 29.

The reusable lancet device 10 of the present invention, as recited, includes a relatively small number of distinct pieces. The use of such a small number of pieces enables quick and substantially inexpensive manufacturing of the reusable lancet device 10 of the present invention, thereby making a cost effective product which can be available to the public without compromising safety.

During use, the needle holding member 30 is moved to its retracted, cocked position by removing the cap segment 50, placing the disposable lancet 60 within the needle holding member 30, and pushing the disposable lancet 60 and accordingly the needle holding member 30 into the housing 20 until the trigger engages. Once properly positioned, the protective cap 62 can be removed from the disposable lancet 60 so as to expose the point 61, and the cap segment 50 is replaced thereover. Due to the triangular shape, the cap segment 50 will securely and properly fit over the housing 20 no matter which orientation a user utilizes to push the cap segment 50 onto the housing 20. After a single use of the disposable lancet 60, the cap 50 is removed, the disposable lancet 60 is removed and discarded appropriately, and the reusable lancet device 10 of the present invention is ready for an additional use.

When a user wishes to adjust the length of the needle holding member 30, the cap segment 50 is removed. The proximal segment 38 and the proximal central segment 31 are rotated relative to each other by use of the threaded connection such that the protruding element 76 snaps into and out of grooves 78. To fix the length of the needle holding member, the user leaves the protruding element 76 engaged in a particular groove 78. The cap segment 50 is then put back on the housing to cover the length adjustment mechanism 70 so that the reusable lancet device is again ready for use. At this point, it should be noted that once the user adjusts the penetration depth to an appropriate depth, the penetration depth usually does not need to be adjusted again.

Figure 10:
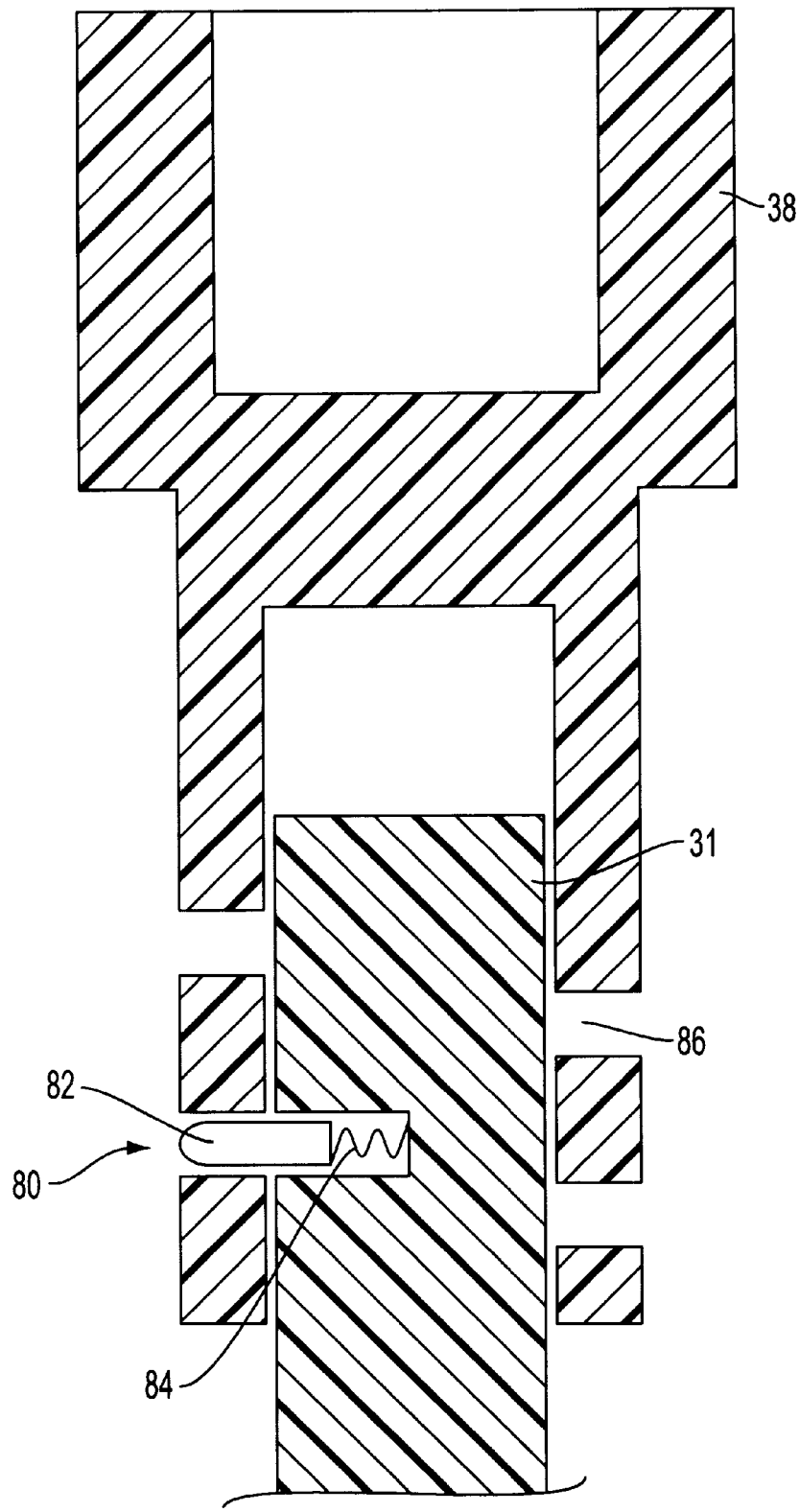
FIG. 10 is a cross-sectional view of an embodiment for adjusting the length of the needle holding member involving a spring-biased element for engaging holes.

FIG. 10 shows another embodiment for adjusting the length of the needle holding member. The proximal central segment 31 is provided with a spring-biased cylindrical element 80 comprised of a protruding element 82 and a spring 84. Although the spring-biased element 80 is shown as being cylindrical, other shapes such as square may be useful The spring-biased element 80 is perpendicular to an axis of the proximal central segment 31. Of course, the spring-biased element 80 does not need to be exactly perpendicular to the proximal central segment 31.

The proximal segment 38 is provided with a plurality of holes 86. The holes 86 are located at different positions with respect to the axial length of the proximal segment 38. For example, the holes 86 may be located at different axial and radial positions so as to form a spiral effect about the proximal segment 38. Instead of holes 86, the proximal segment 38 could be provided with recesses for the spring-biased element 80 to engage.

The spring-biased element 80 and the holes 86 are designed to engage each other to fix the length of the needle holding member 30. The length of the needle holding member 30 may be adjusted by changing the hole 86 in which the spring-biased element 80 is engaged. The embodiment shown in FIG. 10 may be modified such that the proximal segment is provided with the spring-biased element and the proximal central segment is provided with the holes.

Figure 11:
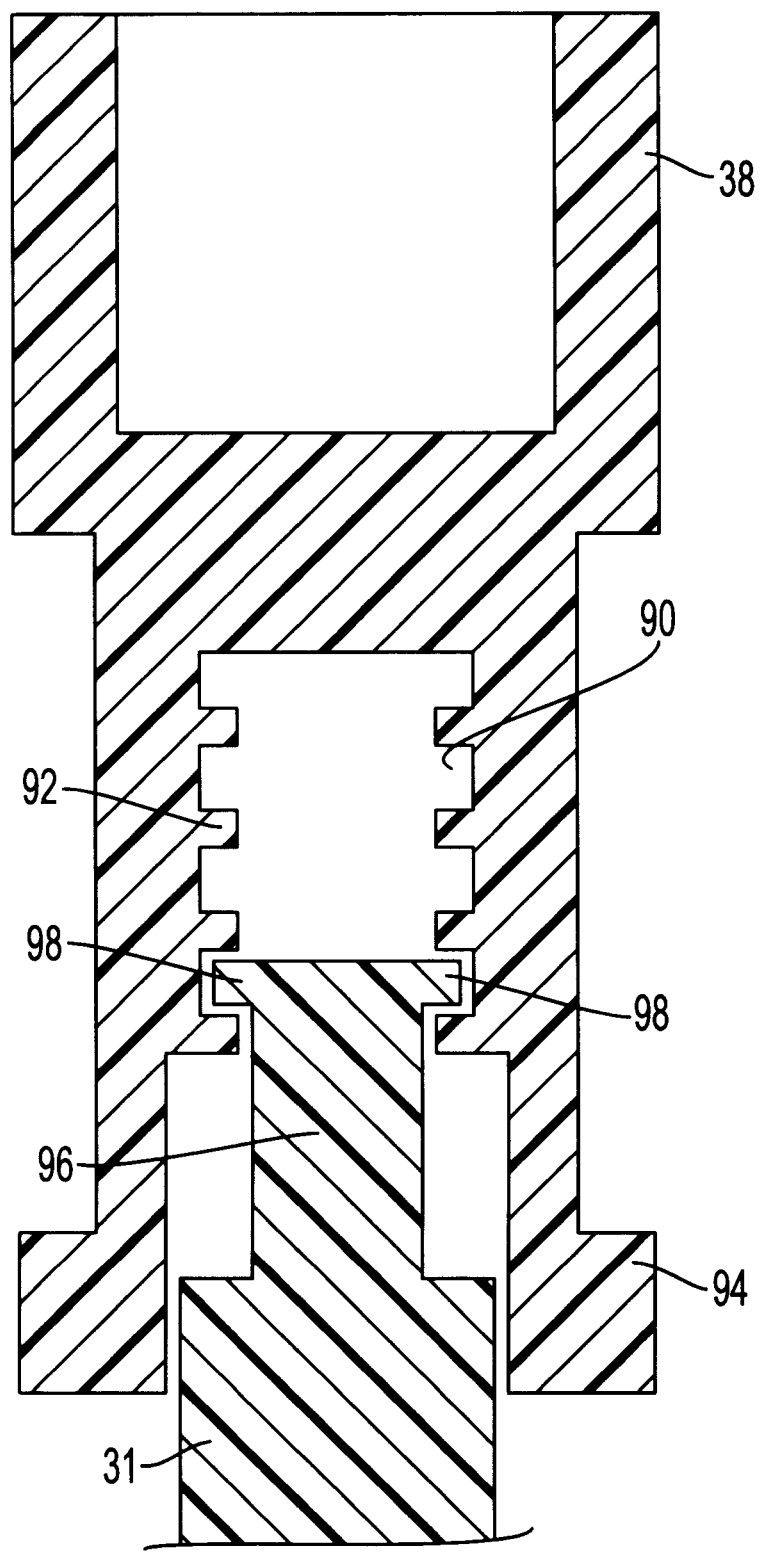
FIG. 11 is a cross-sectional view of an embodiment for adjusting the length of the needle holding member involving a proximal segment having grooves and a proximal central segment having ridges for engaging the grooves of the proximal segment.

FIG. 11 illustrates another embodiment for adjusting the length of the needle holding member 30. The proximal segment 38 has an interior provided with a plurality of grooves 90 formed by ridges 92. The proximal segment 38, which is formed of a resilient material, also has a pair of handles 94 on a distal end which can be grabbed by a user to separate the sides having the grooves 90.

The proximal central segment 31 includes a neck 96 provided with two ridges 98. The ridges 98 are designed to engage the grooves 90 of the proximal segment 38.

The length of the needle holding member 30 is adjusted by changing the groove 90 in which the ridges 98 of the neck 96 are engaged. To facilitate changing the length, a user may grab handles 94 to increase the distance between the grooves 90.

The embodiment shown in FIG. 11 may be modified to form the ridges as a single ridge which forms a circle about the top of the head of the proximal central segment. In this modified embodiment, the groove in which the ridge is engaged is changed by forcing the ridge from one groove to another groove. Accordingly, handles are omitted from this modified embodiment. The ridges, of course, may also number greater than two.

Figure 12:
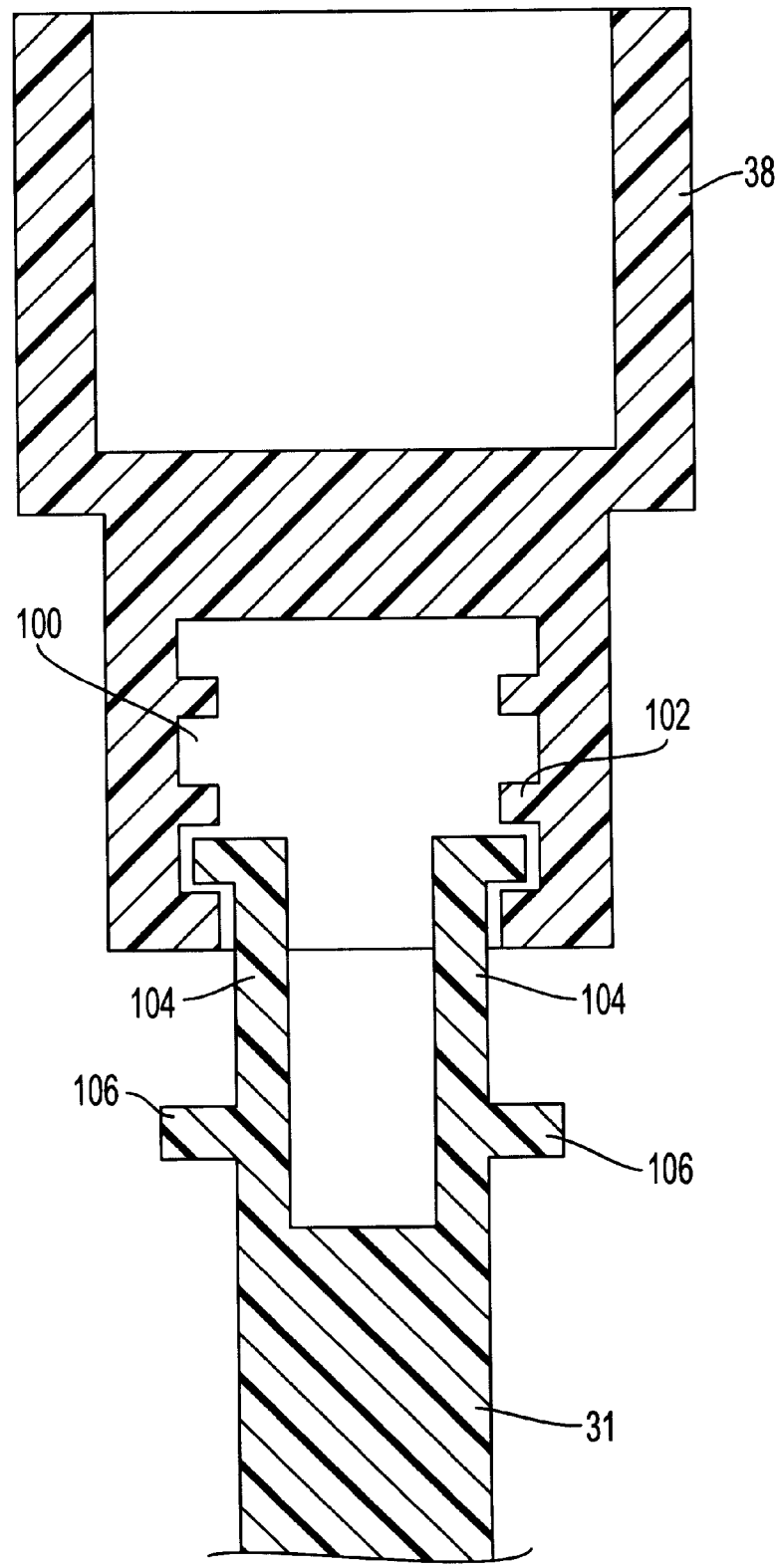
FIG. 12 is a cross-sectional view of an embodiment for adjusting the length of the needle holding member involving a proximal segment having grooves and a proximal central segment having a pair of leaf springs for engaging the grooves of the proximal segment.

FIG. 12 shows another embodiment for adjusting the length of the needle holding member. The proximal segment 38 has an interior which is provided with a plurality of grooves 100 formed by ridges 102.

Figure 13:
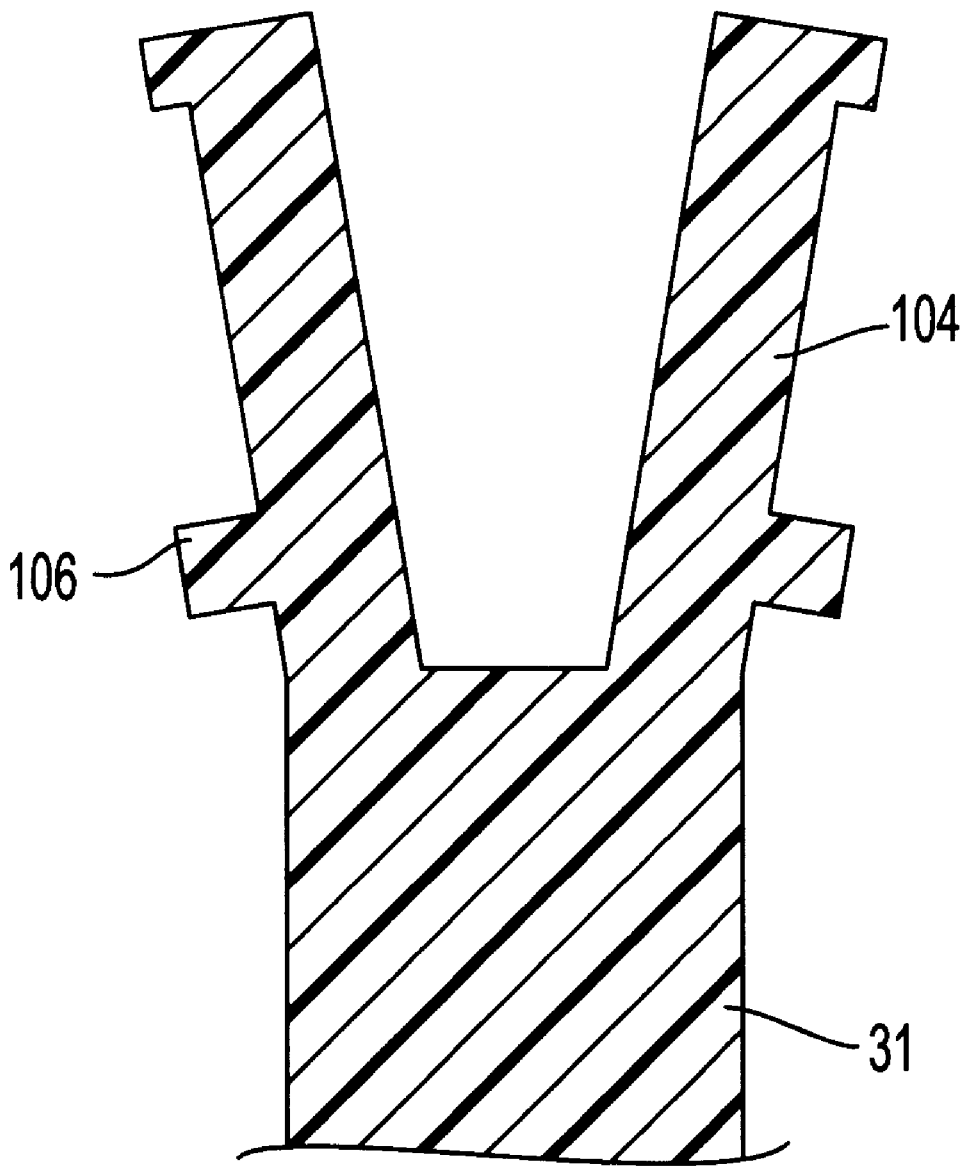
FIG. 13 is a cross-sectional view of the proximal central segment of FIG. 12 before insertion into the proximal segment.

The proximal central segment 31 has a pair of leaf springs 104 for engaging the grooves 100. Although a pair of leaf springs 104 are shown, a different number of leaf springs may be used such as one or more. A distal end of each leaf spring is preferably provided with a pair of buttons 106 which allow a user to push the leaf springs 104 together. FIG. 13 shows the proximal central segment 31 as molded to show the direction in which the leaf springs 104 are biased. Although the leaf springs 104 are shown as being made of a resilient plastic, the leaf springs may be a separate piece formed of a metal such as stainless steel or brass.

The length of the needle holding member 30 is adjusted by changing the groove 100 in which the leaf springs 104 are engaged. To facilitate changing the length, a user squeezes the leaf springs 104 together through use of buttons 106 to reduce the distance between the leaf springs 104.

In another group of embodiments, the length of the needle holding member may be fixed and the length of the housing is adjusted to adjust the penetration depth of the lancet. In this group of embodiments, the device is similar to that disclosed in U.S. Pat. No. 5,464,418 to SCHRAGA, the disclosure of which is herein incorporated by reference in its entirety, except for the housing length adjustment mechanisms as discussed below. Thus, in this group of embodiments, the needle holding member includes a distal segment, a central segment, and the proximal segment.

Figure 14:
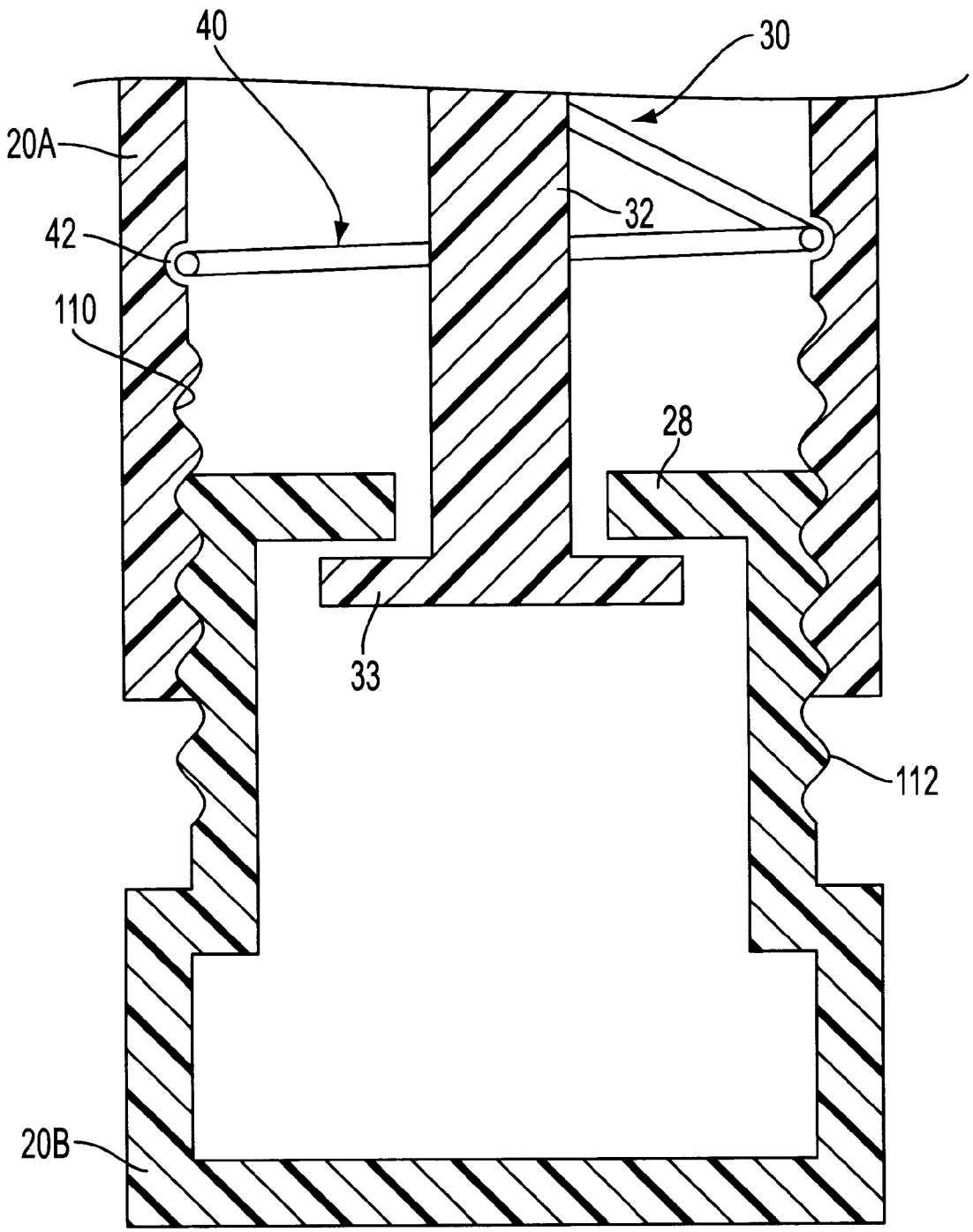
FIG. 14 is a cross-sectional view of an embodiment for adjusting the length of the housing involving a threaded upper housing which engages a threaded lower housing having a guide collar for engaging a flanged end of the needle holding member, wherein the needle holding member is shown in its fully extended position.

FIG. 14 illustrates one embodiment for adjusting the housing length. In FIG. 14, the needle holding member 30 is shown in its fully extended position. The housing 20 comprises an upper housing 20A and a lower housing 20B. The upper housing 20A includes internal threads 110, and the lower housing 20B includes external threads 112. The position of the upper housing 20A relative to the lower housing 20B may be adjusted via rotation about threads 110, 112.

The guide collar 28 of this embodiment is provided on the lower housing 20B. The flanged end 33 of the distal segment 32 of the needle holding member cooperates with the guide collar in the same manner as described above. Thus, the guide collar 28 engages the flanged end 33 provided on the needle holding member 30 to thereby limit the amount of travel of the needle holding member 30. Thus, the guide collar 28 of the lower housing 20A limits the extent to which the needle holding member 30 extends in its fully extended position such that adjusting the position of the guide collar 28 adjusts the penetration depth.

Figure 15:
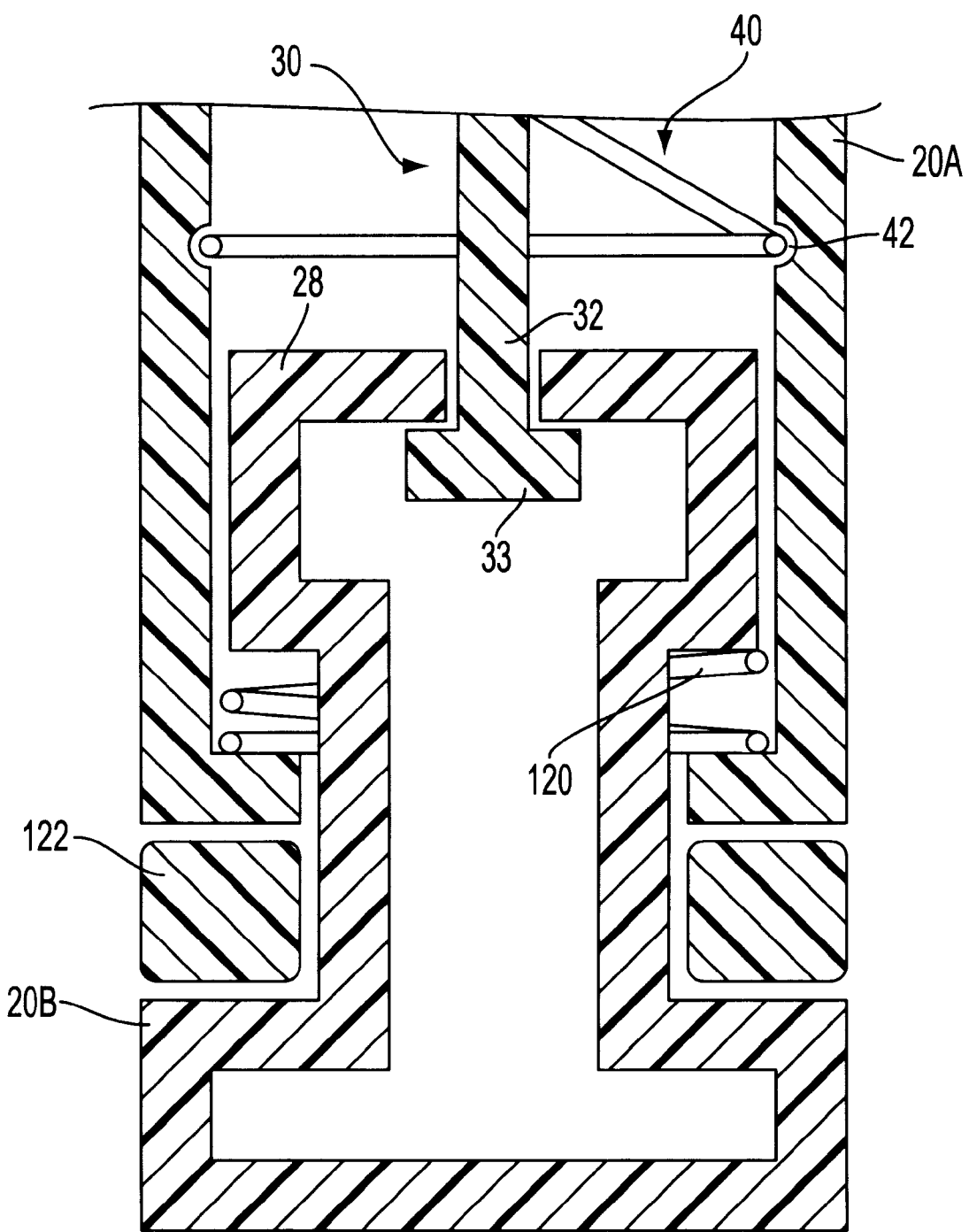
FIG. 15 is a cross-sectional view of an embodiment for adjusting the length of the housing involving a spring which biases an upper housing and a lower housing against a spacer, wherein the needle holding member is shown in its fully extended position.

FIG. 15 illustrates another embodiment for adjusting the length of the housing. In FIG. 15, the needle holding member 30 is shown in its fully extended position. The housing 20 comprises an upper housing 20A and a lower housing 20B. A spring 120 is disposed between the upper housing 20A and the lower housing 20B to bias the housing 20 into a short length. Spacers 122 of varying lengths may be inserted between the spring-biased members of the housing 20 to set the length of the housing 20 at desired lengths. The spacers 122 may be formed of most any material but are preferably formed of rubber or nylon. Alternatively, the spacers may be in the form of C-clip spacers.

The lower housing 20B includes a guide collar 28 for engaging a flanged end 33 of the needle holding member 30 to thereby limit the amount of travel of the needle holding member 30. Thus, similar to the embodiment shown in FIG. 14, adjusting the position of the guide collar 28 limits the extent to which the needle holding member 30 extends in its fully extended position.

Figure 16:
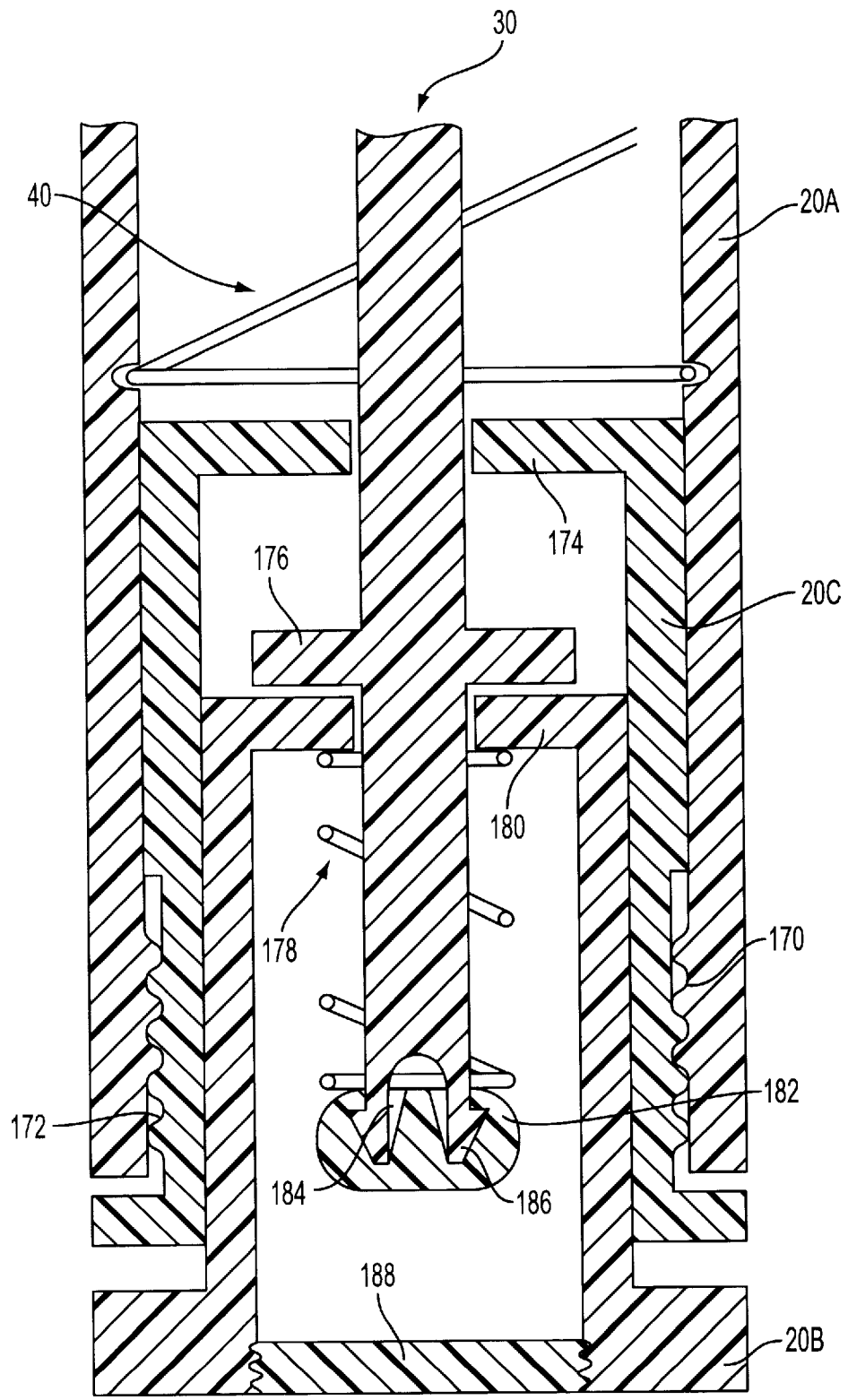
FIG. 16 is a cross-sectional view of an embodiment for adjusting the length of the housing, involving a spring which biases a needle holding member in a retracted position and threaded members for adjusting the length of the housing, wherein the needle holding member is shown in its retracted position.

FIG. 16 illustrates an yet another embodiment for adjusting the length of the housing. In FIG. 16, the needle holding member 30 is shown in its fully retracted position. The housing 20 comprises an upper housing 20A, a lower housing 20B, and a middle housing 20C. The upper housing 20A includes internal threads 170 which cooperate with external threads 172 on the middle housing 20C for adjusting the length of the housing 20. Thus, adjusting the length of the housing involves screwing or unscrewing the lower housing 20B relative to the middle housing 20C.

Adjusting the length of the housing 20 adjusts the position of a guide collar 174 located on the middle housing 20C. The guide collar 174 is designed to cooperate with a flange 176 located on the needle holding member 30 to thereby limit the amount of travel of the needle holding member 30. Thus, similar to the embodiments of FIGS. 14 and 15, adjusting the position of the guide collar 174 limits the extent to which the needle holding member 30 extends in its fully extended position.

A coil spring 178 is disposed between a lower housing guide collar 180 and a lock retainer 182. The lock retainer 182 includes two holes 184 into which two fingers 186 of the needle holding member 30 are inserted and snapped into place. The lower housing 20B includes a cap 188 which provides access into the lower housing 20B. Access into lower housing 20B facilitates positioning of coil spring 178 during assembly.

During assembly, the needle holding member 30 is inserted into lower housing 20B. After the coil spring 178 is placed around the needle holding member 30, the lock retainer is attached to the needle holding member 30 to hold the coil spring 178 in position. After this assembly, the cap 188 is inserted into the lower housing 20B to prevent access to the interior of the lower housing 20B.

Once the device has been assembled, to cock the needle holding member 30, the lower housing 20B is pulled out of the middle housing 20C to pull the needle holding member 30 until a trigger, not shown, which is similar to the trigger of the embodiment shown in FIGS. 1–7, engages the needle holding member 30. Upon release of the lower housing 20B, the coil spring 178 biases the lower housing 20B back into the middle housing 20C.

In yet another group of embodiments, the penetration depth is adjusted by rotating the housing relative to the needle holding member to cause the needle holding member to engage different stops. The stops are arranged such that aligning the needle holding member with different stops results in different penetration depths. In this group of embodiments, the needle holding member may be of fixed length with a distal segment, a central segment, and a proximal segment as disclosed in U.S. Pat. No. 5,464,418 to SCHRAGA, the disclosure of which is herein incorporated by reference in its entirety.

Figure 17:
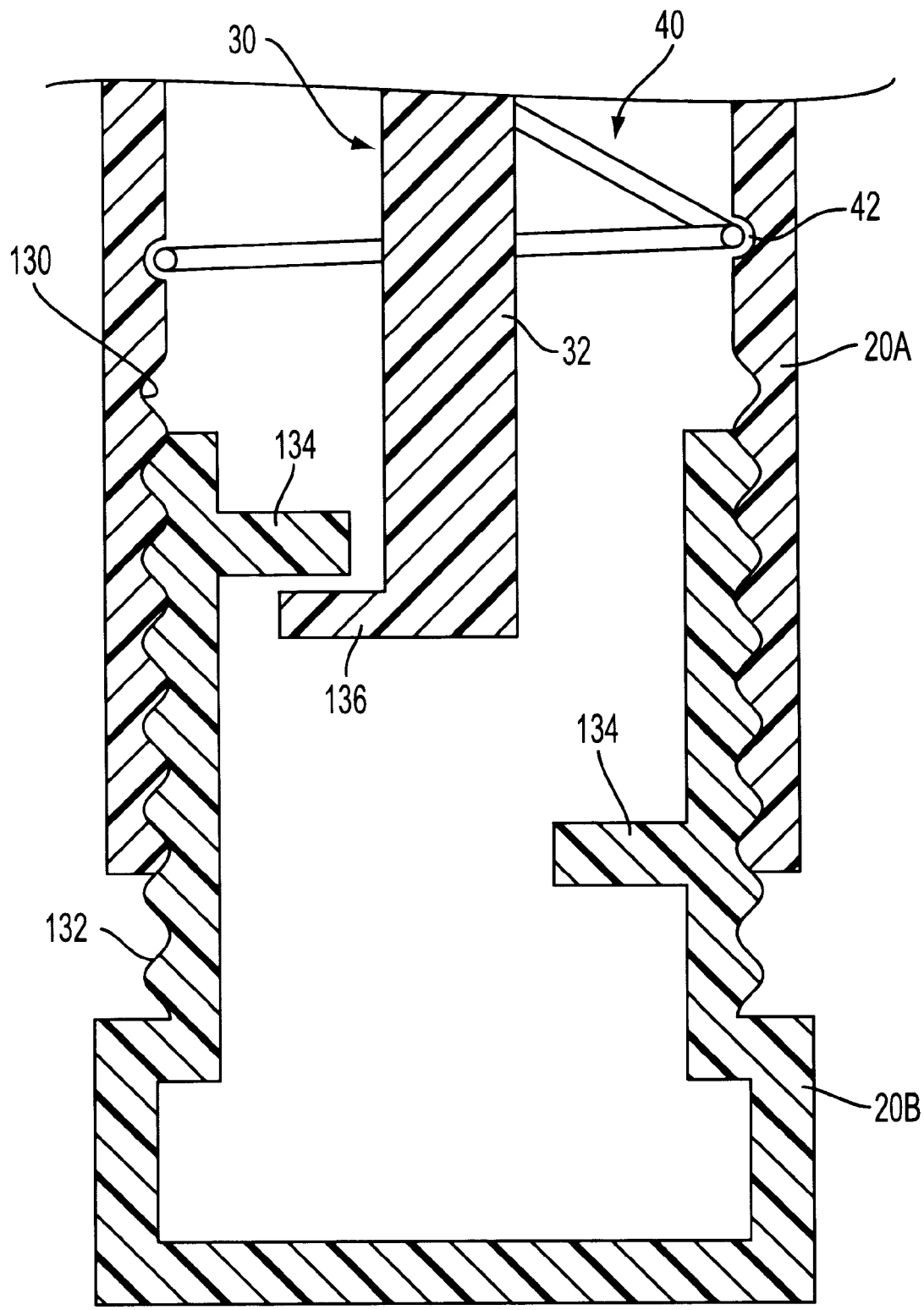
FIG. 17 is a cross-sectional view of an embodiment for adjusting which stop is engaged involving a threaded upper housing which engages a threaded lower housing having a plurality of stops for engaging a finger of a needle holding member, wherein the needle holding member is shown in its fully extended position.

FIG. 17 illustrates an embodiment for adjusting the penetration depth by changing which stop is engaged by rotating a portion of the housing 20 relative to the needle holding member 30. The housing comprises an upper housing 20A and a lower housing 20B. The upper housing 20A includes internal threads 130, and the lower housing 20B includes external threads 132. The position of the upper housing 20A relative to the lower housing 20B may be adjusted via rotation about threads 130, 132.

The lower housing 20B includes a plurality of stops 134 for limiting the travel of the needle holding member 30. The stops 134 are located at different radial positions and at different axial positions to preferably form a spiral staircase effect on the interior of the lower housing 20B.

The needle holding member 30 includes a finger 136 for engaging one of these stops 134 at a time. Rotation of the upper housing 20A and lower housing 20B relative to each other causes the finger 136 of the needle holding member 30 to become aligned with different stops 134, one at a time. Since the stops 134 are located at different positions relative to the axial length of the lower housing 20B, the amount of travel of the needle holding member 30 is limited to different lengths. Thus, changing which stop engages the finger 136 of the needle holder member 30 adjusts the extent to which the needle holding member 30 extends in its fully extended position such that the penetration depth is adjusted.

Figure 18:
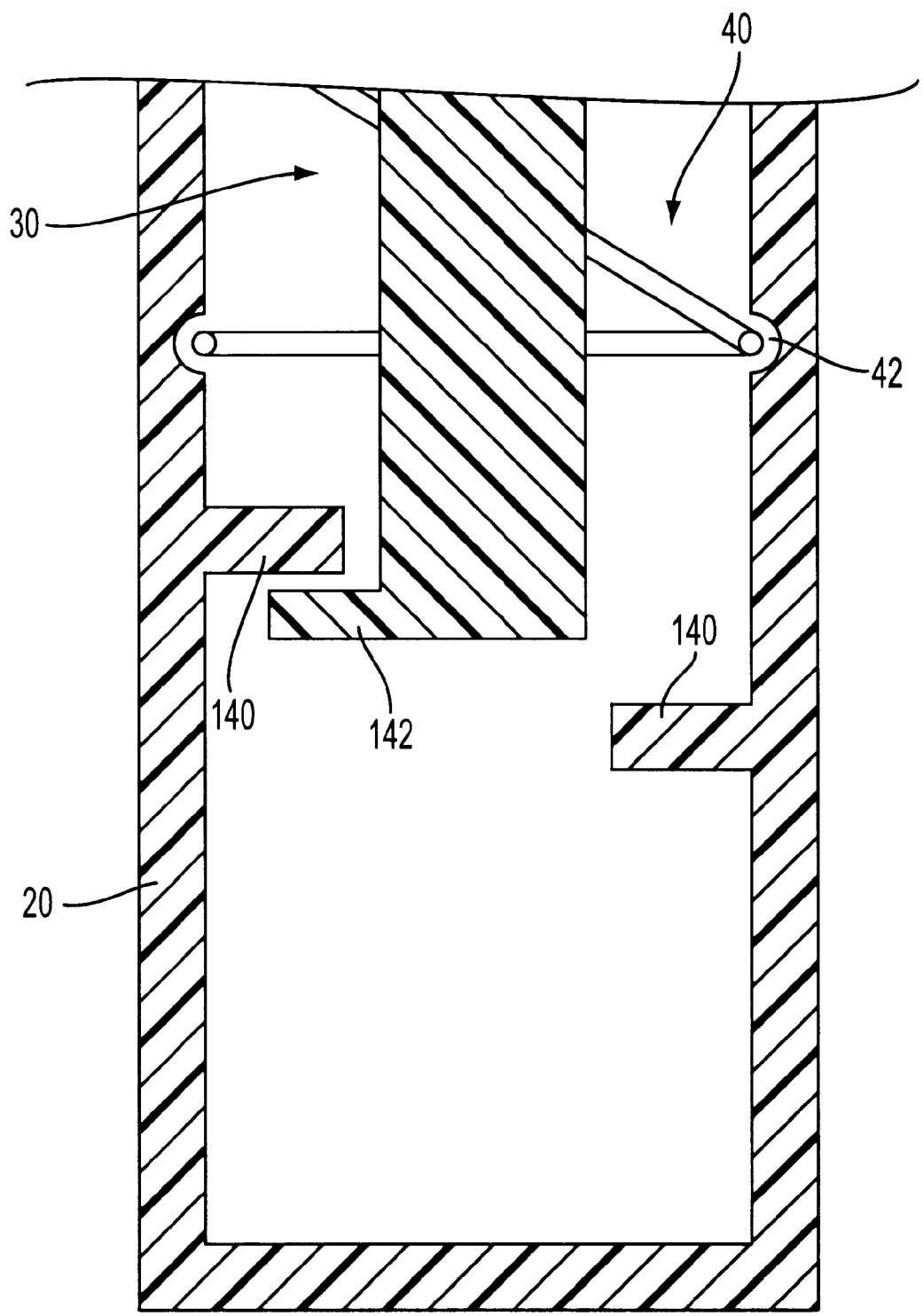
FIG. 18 is a cross-sectional view of an embodiment for adjusting which stop is engaged involving a housing having a plurality of stops and a rotatable needle holding member which has a finger for engaging the plurality of stops one at a time, wherein the needle holding member is shown in its fully extended position.

FIG. 18 illustrates another embodiment for adjusting which stop is engaged, wherein rotation of the needle holding member relative to the housing adjusts the penetration depth. A housing 20 includes a plurality of stops 140 for limiting the travel of the needle holding member 30. The stops 140 are located at different radial positions and at different axial positions to preferably form a spiral staircase effect on the interior of the housing 20.

The needle holding member 30 includes a finger 142 for engaging one of these stops 140 at a time. Rotation of the needle holding member 30 relative to the housing 20 causes the finger 142 of the needle holding member 30 to become aligned with different stops 140, one at a time. Since the stops 140 are located at different positions relative to the axial length of the housing 20, the amount of travel of the needle holding member 30 is limited to different lengths. Thus, changing which stop 140 engages the finger 142 of the needle holder member 30 adjusts the extent to which the needle holding member 30 extends in its fully extended position to adjust the penetration depth.

In yet another group of embodiments, the reusable lancet device is similar to that disclosed in U.S. Pat. No. 5,464,418 to SCHRAGA, the disclosure of which is herein incorporated by reference in its entirety, and includes a needle holding member which includes a distal segment, a central segment, and a proximal segment. In this group of embodiments, the structure of the proximal segment for holding the disposable lancet includes a cavity. The bottom of this cavity includes a member whose location may be adjusted. By adjusting the location of this member, the depth of the cavity is adjusted such that the distance which the lancet extends out of the cavity is adjusted to adjust the penetration depth.

Figure 19:
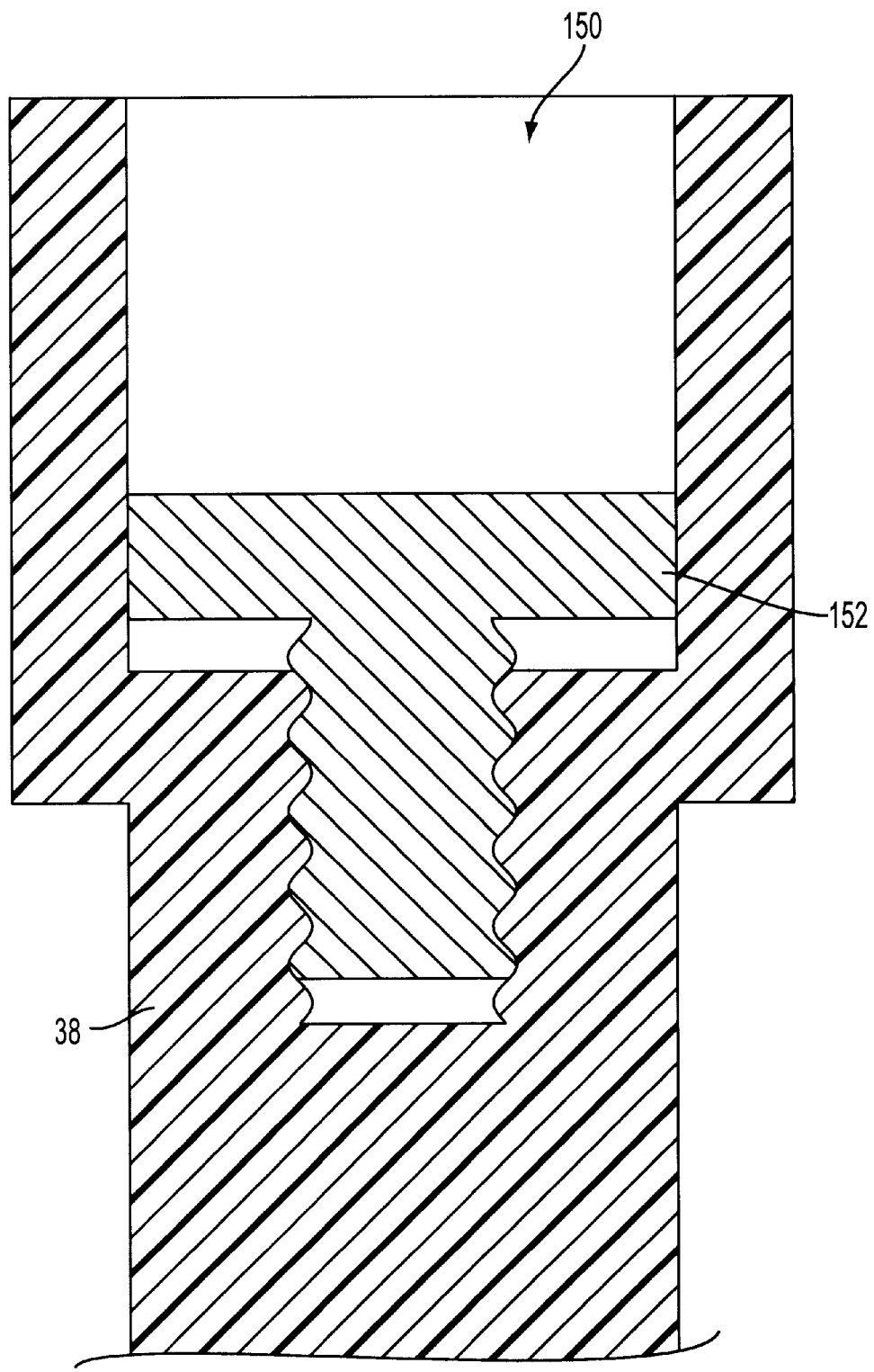
FIG. 19 is a cross-sectional view of an embodiment for adjusting a cavity depth involving an adjustable bottom member which is a screw.

FIG. 19 illustrates an embodiment for adjusting the cavity depth. A proximal segment 38 of the needle holding member 30 includes a cavity 150 for holding a disposable lancet 60. The shape of the cavity 150 is preferably round, but is designed to accept a disposable lancet. The bottom of the cavity 150 is formed by an adjustable bottom member such as a screw 152. By screwing or unscrewing the screw 152 before the disposable lancet 60 is placed in the cavity 150, the depth of the cavity 150 may be adjusted to change the distance that the disposable lancet 60 extends out of the cavity 150. By changing the distance that the disposable lancet 60 extends out of the cavity 150, the penetration depth is adjusted.

Figure 20:
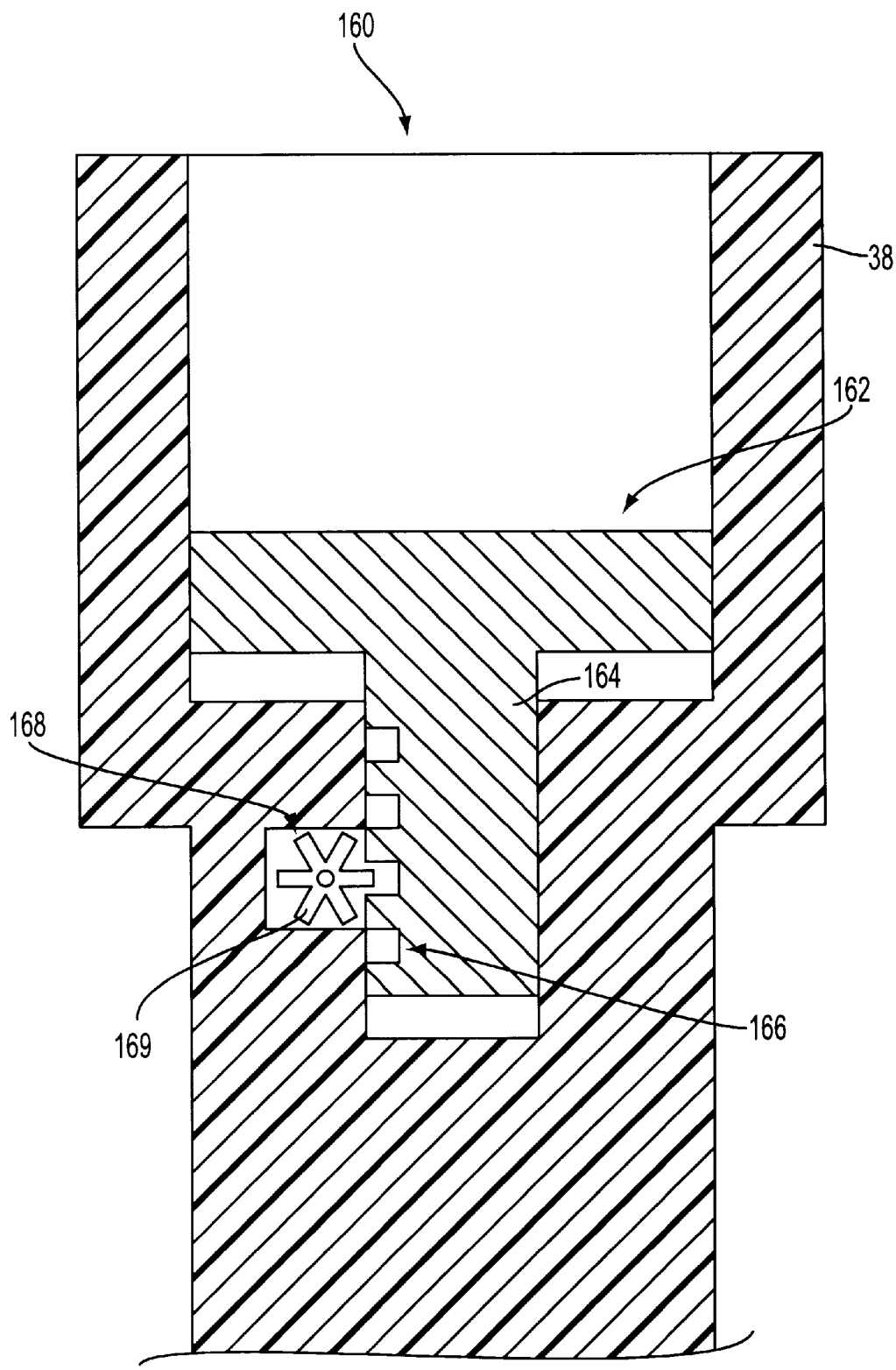
FIG. 20 is a cross-sectional view of an embodiment for adjusting a cavity depth involving an adjustable bottom member which is adjusted by use of a rack and pinion.

FIG. 20 shows another embodiment for adjusting the cavity depth. A proximal segment 38 of the needle holding member includes a cavity 160 for holding a disposable lancet 60. The preferred shape of cavity 160 is round. The bottom of the cavity 160 is formed by an adjustable bottom member which comprises a nail 162 having a tail 164 provided with a rack 166. The proximal segment 38 of the needle holding member 30 also includes a turn-key 168 disposed perpendicular to the nail 162, and a head (not shown) which is exposed on the exterior of the proximal segment 38. The turn-key 168 is a screw provided with a pinion 169 at a distal end for engaging the rack 166 of the nail 162. By rotating the turn-key 168, the location of the adjustable bottom member may be changed to adjust the depth of the cavity 160 of the proximal segment. Changing the location of the adjustable bottom member changes the distance that the disposable lancet 60 extends out of the cavity 160 to thereby adjust the penetration depth. Once the height of the adjustable bottom member is set appropriately, the rotational position of the turn-key 168 could be locked by changing the vertical position of the turn-key 168 such that the pinion 169 engages a surface or a notch (not shown in the drawings) of the proximal segment 38. The turn-key may also interact with the adjustable bottom member in other manners in which rotational motion in one direction may be converted into translational motion in a perpendicular direction, such as a worm gear arrangement in which the turn key and the adjustable bottom member have threads which interact with each other.

Preferably, the components of the reusable lancet device of the present invention are made of plastic. Examples of desirable plastics include polypropylene (PP), polyvinyl chloride (PVC), acrylonitrile butadiene styrene (ABS), nylon, linear polyoxymethylene-type acetal resin, e.g., "DELRIN", and polycarbonate (PC), e.g., "LEXAN".

To assist in determining the penetration depth of the lancet, indicia can be included on members that change position relative to each other when the penetration depth is adjusted. For example, as illustrated in FIG. 1, indicia 87 and 88 can be included on proximal segment 38 and proximal central segment 31. The indica can comprise elements which can be viewed by shape and/or color, such as reference numerals, letters, lines and geometric shapes. Moreover, the indica may be sensed by touch, such as raised elements, including braille. As illustrated, indica 87 includes a line and indica 88 includes reference numerals. The reference numerals can be numbers, such as from 0 to 5, with 0 being no penetration to 5 being maximum penetration.

While the invention has been described in connection with certain preferred embodiments so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

What is claimed:

1. A lancet device, comprising:
   a housing;
   a cap for covering the housing and for positioning the lancet device relative to a skin surface;
   a needle holding member for holding a lancet, the needle holding member being at least partially contained within the housing;
   a biasing element for biasing the needle holding member toward an extended position;
   a trigger for releasing the needle holding member from a retracted position; and
   a travel adjustment mechanism capable of adjusting a length of travel of said needle holding member, said travel adjustment mechanism being completely positioned inside at least one of said housing and said cap during at least a portion of the length of travel of said needle holding member, said travel adjustment mechanism comprising a first component and a second component.

2. The lancet device of claim 1, wherein the needle holding member comprises the first component and the second component of the travel adjustment mechanism, and wherein the travel adjustment mechanism comprises a threaded connection between the first component and the second component.

3. The lancet device of claim 2, wherein the travel adjustment mechanism further comprises a protruding element on one of the first component and the second component, and grooves on the other of the first component and the second component, the protruding element being capable of engaging the grooves.

4. The lancet device of claim 3, wherein the protruding element comprises a nipple.

5. The lancet device of claim 3, wherein the protruding element comprises a spring-biased ball.

6. The lancet device of claim 1, wherein the needle holding member comprises the first component and the second component of the travel adjustment mechanism, and wherein the travel adjustment mechanism comprises a spring-biased element on one of the first component and the second component, and a plurality of recesses in the other of the first component and the second component, the spring-biased element being capable of engaging the recesses.

7. The lancet device of claim 1, wherein the needle holding member comprises the first component and the second component of the travel adjustment mechanism, and wherein the travel adjustment mechanism comprises grooves in one of the first component and the second component, and a ridge on the other of the first component and the second component, the ridge being capable of engaging the grooves.

8. The lancet device of claim 1, wherein the needle holding member comprises the first component and the second component of the travel adjustment mechanism, and wherein the travel adjustment mechanism comprises grooves in one of the first component and the second component, and at least one leaf spring on the other of the first component and the second component, the at least one leaf spring being capable of engaging the grooves.

9. The lancet device of claim 1, wherein the travel adjustment mechanism is positioned within said housing and said cap during the length of travel of said needle holding member.

10. A lancet device, comprising:
a housing;
a cap for covering the housing and for positioning the lancet device relative to a skin surface;
a needle holding member for holding a lancet, the needle holding member being at least partially contained within the housing, a length of the needle holding member being adjustable for adjusting a penetration depth of a needle within the needle holding member, the needle holding member comprising a first component and a second component;
a biasing element for biasing the needle holding member toward an extended position; and
a trigger for releasing the needle holding member from a retracted position.

11. The lancet device of claim 10, wherein the needle holding member comprises a threaded connection between the first component and the second component.

12. The lancet device of claim 11, wherein the needle holding member comprises a protruding element on one of the first component and the second component, and grooves on the other of the first component and the second component, the protruding element being capable of engaging the grooves.

13. The lancet device of claim 12, wherein the protruding element comprises a nipple.

14. The lancet device of claim 12, wherein the protruding element comprises a spring-biased ball.

15. The lancet device of claim 10, wherein the needle holding member comprises a spring-biased element on one of the first component and the second component, and a plurality of recesses in the other of the first component and the second component the spring-biased element being capable of engaging the recesses.

16. The lancet device of claim 10, wherein the needle holding member comprises grooves in one of the first component and the second component, and a ridge on the other of the first component and the second component, the ridge being capable of engaging the grooves.

17. The lancet device of claim 10, wherein the needle holding member comprises grooves in one of the first component and the second component, and at least one leaf spring on the other of the first component and the second component, the at least one leaf spring being capable of engaging the grooves.

18. A lancet device, comprising:
a housing;
a cap for covering the housing and for positioning the lancet device relative to a skin surface;
a needle holding member comprising a cavity having a depth for holding a lancet, the needle holding member being at least partially contained within the housing;
a biasing element for biasing the needle holding member toward an extended position;
a trigger for releasing the needle holding member from a retracted position; and
an adjustable member disposed within the cavity of the needle holding member for adjusting the cavity depth of the needle holding member.

19. The lancet device of claim 18, wherein the adjustable member comprises a screw.

20. The lancet device of claim 18, wherein the needle holding member comprises a turn-key having a pinion, and wherein the adjustable member comprises a nail having a tail which has a rack for engaging the pinion.

21. A lancet device, comprising:
a housing;
a cap for covering the housing and for positioning the lancet device relative to a skin surface;
a needle holding member for holding a lancet, the needle holding member being at least partially contained within the housing;
a biasing element for biasing the needle holding member toward an extended position;
a trigger for releasing the needle holding member from a retracted position; and
means for adjusting a penetration depth of a lancet by adjusting a travel distance of the needle holding member, the means for adjusting the penetration depth being capable of being completely contained inside the housing and the cap, the means for adjusting the penetration depth comprising a first component and a second component.

* * * * *